(12) United States Patent
Joshi et al.

(10) Patent No.: US 11,365,225 B2
(45) Date of Patent: Jun. 21, 2022

(54) METHOD OF MAKING RECOMBINANT SILK AND SILK-AMYLOID HYBRID PROTEINS USING BACTERIA

(71) Applicant: President and Fellows of Harvard College, Cambridge, MA (US)

(72) Inventors: Neel Satish Joshi, Somerville, MA (US); Peter Quoc Nguyen, Malden, MA (US)

( * ) Notice: Subject to any disclaimer, the term of this patent is extended or adjusted under 35 U.S.C. 154(b) by 880 days.

(21) Appl. No.: 15/776,998

(22) PCT Filed: Nov. 18, 2016

(86) PCT No.: PCT/US2016/062820
§ 371 (c)(1),
(2) Date: May 17, 2018

(87) PCT Pub. No.: WO2017/087827
PCT Pub. Date: May 26, 2017

(65) Prior Publication Data
US 2020/0291078 A1    Sep. 17, 2020

Related U.S. Application Data

(60) Provisional application No. 62/257,405, filed on Nov. 19, 2015.

(51) Int. Cl.
| | | |
|---|---|---|
| C07K 19/00 | (2006.01) | |
| C07K 14/435 | (2006.01) | |
| C12N 15/70 | (2006.01) | |
| C07K 14/47 | (2006.01) | |
| C07K 14/78 | (2006.01) | |
| C12N 1/20 | (2006.01) | |
| C12R 1/19 | (2006.01) | |

(52) U.S. Cl.
CPC ........ *C07K 14/43518* (2013.01); *C07K 14/47* (2013.01); *C07K 14/78* (2013.01); *C07K 2319/036* (2013.01); *C07K 2319/10* (2013.01); *C12N 1/205* (2021.05); *C12R 2001/19* (2021.05)

(58) Field of Classification Search
CPC ............ C07K 2319/10; C07K 2319/00; C07K 14/43518
See application file for complete search history.

(56) References Cited

U.S. PATENT DOCUMENTS

| | | | |
|---|---|---|---|
| 10,889,823 B2 * | 1/2021 | Arrieumerlou | ......... A61P 37/00 |
| 10,906,947 B2 * | 2/2021 | Kittleson | ............. C07K 14/395 |
| 2001/0042255 A1 * | 11/2001 | Karatzas | ............ C12N 15/8509 800/4 |
| 2006/0246539 A1 | 11/2006 | Weiner et al. | |
| 2012/0225453 A1 | 9/2012 | Withers, III et al. | |
| 2014/0343251 A1 | 11/2014 | Schwarz et al. | |

FOREIGN PATENT DOCUMENTS

| | | |
|---|---|---|
| EP | 2668962 A1 | 12/2013 |
| WO | 2008/019183 A2 | 2/2008 |
| WO | 2014/176311 A1 | 10/2014 |

OTHER PUBLICATIONS

International Search Report for Application No. PCT/US2016/062820, dated Feb. 16, 2017. 3 pages.
International Preliminary Report on Patentability for Application No. PCT/US2016/062820, dated May 31, 2018. 17 pages.

\* cited by examiner

*Primary Examiner* — Maryam Monshipouri
(74) *Attorney, Agent, or Firm* — Foley Hoag LLP; Dana M. Gordon; Jack Rosa

(57) ABSTRACT

Methods of making recombinant secretion of silk and silk-amyloid proteins using bacteria are provided.

8 Claims, 7 Drawing Sheets
Specification includes a Sequence Listing.

Fig. 3A Golden Silk Orb-Weaving Spider N. clavipes Repetitive Silk Domain

[MMMM] = GRGGLGGQGAGMAAAAMGGAGQGGYGGLGSQGTS (SEQ ID NO: 3)

METHOD OF MAKING RECOMBINANT SILK AND SILK-AMYLOID HYBRID PROTEINS USING BACTERIA

RELATED APPLICATIONS

This application is a 35 U.S.C. § 371 national stage filing of International Application No. PCT/US2016/062820, filed on Nov. 18, 2016, which in turn claims priority to U.S. Provisional Application No. 62/257,405, filed on Nov. 19, 2015. The entire contents of each of the foregoing applications are expressly incorporated herein by reference in their entireties.

GOVERNMENT SUPPORT

This invention was made with government support under 1420570 awarded by the National Science Foundation (NSF). The government has certain rights in the invention.

SEQUENCE LISTING

The instant application contains a Sequence Listing which has been submitted electronically in ASCII format and is hereby incorporated by reference in its entirety. Said ASCII copy, created on Nov. 17, 2016, is named 2016-11-17_117823-13120_ST25.TXT and is 818 KB in size.

FIELD

The technology described herein relates to the engineering of a polypeptide secretion system, exogenous nucleic acids encoding a recombinant protein, proteins that include a periplasmic translocation signal sequence, an outer membrane secretion signal sequence, engineered silk fibroin domains, and optionally amyloid-based extracellular matrix components produced by engineered bacterial cells.

BACKGROUND

Silks are protein fibers produced by arthropods. Large-scale production methods include cultivation of *Bombyx mori* silkworms. These silks are naturally used as a self-generated biomaterial by a wide variety of insects and are used for a diverse array of functions, such as anchoring and protection of eggs, lining of nests, binding agents for nest construction, sperm transfer, cocoon formation, and prey traps. Silk fibers possess properties of strength and elasticity that make them a highly valuable commodity. Spider silks are five times stronger on a per weight basis than steel and three times tougher than Kevlar®. Griffiths, J. R. & Salanitri, V. R. The strength of spider silk. *J. Mater. Sci.* 15, 491-496 (1980). It has a large extensibility and energy to breakage (toughness) exceeding that of most engineering materials. Gosline, J. M., Guerette, P. A, Ortlepp, C. S. & Savage, K. N. The mechanical design of spider silks: from fibroin sequence to mechanical function. *J. Exp. Biol.* 202, 3295-3303 (1999). It has also been reported that spider silk possesses a thermal conductivity 800 times greater than any other organic material. Huang, X., Liu, G. & Wang, X. New secrets of spider silk: Exceptionally high thermal conductivity and its abnormal change under stretching. *Adv. Mater.* 24, 1482-1486 (2012). Furthermore, spider silk undergoes supercontraction from temperature and pH changes. Guan, J., Vollrath, F. & Porter, D. Two mechanisms for supercontraction in Nephila spider dragline silk. *Biomacromolecules* 12, 4030-4035 (2011). However, since spiders are venomous and cannibalistic, they cannot be easily domesticated on a large scale for spider silk production.

Spider silk and other protein production has been explored in bacteria, yeast, plants, and mammalian cells. See Fahnestock, S. R. & Irwin, S. L. Synthetic spider dragline silk proteins and their production in *Escherichia coli*. *Appl. Microbiol. Biotechnol.* 47, 23-32 (1997); Xia, X.-X. et al. Native-sized recombinant spider silk protein produced in metabolically engineered *Escherichia coli* results in a strong fiber. *Proc. Natl. Acad. Sci.* 107, 14059-14063 (2010); Widmaier, D. M. et al. Engineering the Salmonella type III secretion system to export spider silk monomers. *Mol. Syst. Biol.* 5, 1-9 (2009); Fahnestock, S. R. & Bedzyk, L. A. Production of synthetic spider dragline silk protein in Pichia pastoris. *Appl. Microbiol. Biotechnol.* 47, 33-9 (1997); Yang, J., Barr, L. A., Fahnestock, S. R. & Liu, Z.-B. High yield recombinant silk-like protein production in transgenic plants through protein targeting. *Transgenic Res.* 14, 313-24 (2005); Lazaris, A. Spider Silk Fibers Spun from Soluble Recombinant Silk Produced in Mammalian Cells. *Science* (80). 295, 472-476 (2002); Widmaier, D. M. & Voigt, C. a. Quantification of the physiochemical constraints on the export of spider silk proteins by Salmonella type III secretion. *Microb. Cell Fact.* 9, 78 (2010); Sivanathan, V. & Hochschild, A. Generating extracellular amyloid aggregates using *E. coli* cells. *Genes Dev.* 26, 2659-2667 (2012).

SUMMARY

The present disclosure describes the use of a secretion system within a bacterium to secrete a silk protein, such as a silk fibroin domain. According to certain aspects, a heterologous (e.g., an exogenous or foreign nucleic acid) encoding the silk protein is introduced into a bacterium. The bacterium can proliferate and express the nucleic acid to produce the silk protein which is also secreted by the bacterium. The silk protein may be secreted such that it is unattached from the bacterium and free of the bacterium or it may be attached to the outer surface of the bacterium, such as being a component of a curli fiber. According to one aspect, the silk protein comprises a periplasmic translocation signal sequence which facilitates the transport of the silk protein from the bacterial cytoplasm to the periplasm of the bacterium. According to one aspect, the silk protein comprises an outer membrane secretion signal sequence which facilitates the transport (e.g., export) of the silk protein to the extracellular milieu, i.e., through the outer membrane of the bacterium. According to one aspect, the silk protein comprises both a periplasmic translocation signal sequence and an outer membrane secretion signal sequence. In some embodiments, the periplasmic translocation signal sequence is cleaved off of the silk protein. In some embodiments, the outer membrane signal secretion signal sequence is cleaved-off the silk protein.

Embodiments of the present disclosure are directed to methods of genetically modifying a bacterium to comprise an exogenous nucleic acid that encodes a recombinant protein nonnative to the bacterium for expression within the bacterium. The nonnative recombinant protein is secreted from within the bacterium to outside of the bacterium. The nonnative recombinant protein can also be a non-natural recombinant protein to the extent that it includes domains or molecules that are used by secretion systems within the bacterium to secrete the nonnative recombinant protein.

In one aspect, provided herein is a method of producing a genetically modified bacterium comprising genetically altering a bacterium having one or more genomic nucleic acids encoding a polypeptide secretion system to include an exogenous nucleic acid encoding a recombinant protein including a domain for periplasmic localization, a domain for directing the recombinant protein to the outer membrane for secretion and one or more silk fibroin domains, wherein the exogenous nucleic acid is under operation of a promoter to express the recombinant protein.

In some embodiments, the polypeptide secretion system is a Type VIII secretion system or a HlyA Type 1 secretion system. In some embodiments, the polypeptide secretion system includes a periplasmic secretion system and a system for secretion through the outer membrane of the bacterium. In some embodiments, the polypeptide secretion system includes a periplasmic secretion system and a system for secretion through the outer membrane of the bacterium and wherein the periplasmic secretion system is a Sec system. In some embodiments, the polypeptide secretion system includes a periplasmic secretion system and a system for secretion through the outer membrane of the bacterium and wherein the periplasmic secretion system is a twin-arginine translocation (Tat) system. In some embodiments, the polypeptide secretion system includes a periplasmic secretion system and a system for secretion through the outer membrane of the bacterium and wherein the periplasmic secretion system is a signal recognition particle (SRP) system. In some embodiments, the polypeptide secretion system includes a periplasmic secretion system and a system for secretion through the outer membrane of the bacterium and a domain for periplasmic localization is a Sec domain or a Tat domain or a signal recognition particle domain. In some embodiments, the polypeptide secretion system includes a periplasmic secretion system and a system for secretion through the outer membrane of the bacterium and a domain for periplasmic localization is a component of a Sec system, a component of a Tat system or a component of a signal recognition particle system.

In some embodiments, the polypeptide secretion system includes a periplasmic secretion system and a system for secretion through the outer membrane of the bacterium and wherein the system for secretion through the outer membrane of the bacterium is a N22 system.

In some embodiments, the polypeptide secretion system includes a periplasmic secretion system and a system for secretion through the outer membrane of the bacterium and wherein the system for secretion through the outer membrane of the bacterium is a YebF system.

In some embodiments, the polypeptide secretion system includes a periplasmic secretion system and a system for secretion through the outer membrane of the bacterium and wherein a domain for directing the recombinant protein to the outer membrane for secretion is an N22 domain or a YebF domain.

In some embodiments, the exogenous nucleic acid further encodes the recombinant protein to include one or more of an amyloid domain, an elastin domain or a collagen domain. In some embodiments, the exogenous nucleic acid further encodes the recombinant protein to include a CsgA domain.

In some embodiments, the bacterium is *E. coli*. In some embodiments, the bacterium is non-pathogenic.

In some embodiments, the silk fibrin domain includes the amino acid sequence GRGGLGGQGAGMAAAAAMGGAGQGGYGGLGSQGTS (SEQ ID NO: 3). In some embodiments, the silk fibrin domain includes 4 to 64 repeats of the amino acid sequence (SEQ ID NO: 3)
GRGGLGGQGAGMAAAAAMGGAGQGGYGGLGSQGTS.

In some embodiments, the exogenous nucleic acid further encodes the recombinant protein to include one or more functional proteins. In some embodiments, the exogenous nucleic acid further encodes the recombinant protein to include one or more functional proteins comprising an enzyme, an antibody or a detectable protein.

In one aspect, provided herein is a method for producing one or more silk fibroin domains from a genetically modified bacterium comprising providing the genetically modified bacterium in culture media conditions, wherein the genetically modified bacterium includes one or more genomic nucleic acids encoding a polypeptide secretion system and further including an exogenous nucleic acid encoding a recombinant protein including a domain for periplasmic localization, a domain for directing the recombinant protein to the outer membrane for secretion and the one or more silk fibroin domains, wherein the exogenous nucleic acid is under operation of a promoter to express the recombinant protein, and expressing the exogenous nucleic acid to produce the recombinant protein wherein the recombinant protein is secreted from the bacterium and into the surrounding culture media.

In some embodiments, the bacterium is proliferated to produce a population of bacteria cells expressing the exogenous nucleic acid. In some embodiments, the bacterium is proliferated to produce a population of bacteria cells expressing the exogenous nucleic acid to form a biofilm including the recombinant protein.

In some embodiments, the polypeptide secretion system is a Type VIII secretion system or a HlyA Type 1 secretion system. In some embodiments, the polypeptide secretion system includes a periplasmic secretion system and a system for secretion through the outer membrane of the bacterium. In some embodiments, the polypeptide secretion system includes a periplasmic secretion system and a system for secretion through the outer membrane of the bacterium and wherein the periplasmic secretion system is a Sec system. In some embodiments, the polypeptide secretion system includes a periplasmic secretion system and a system for secretion through the outer membrane of the bacterium and wherein the periplasmic secretion system is a twin-arginine translocation (Tat) system. In some embodiments, the polypeptide secretion system includes a periplasmic secretion system and a system for secretion through the outer membrane of the bacterium and wherein the periplasmic secretion system is a signal recognition particle (SRP) system. In some embodiments, the polypeptide secretion system includes a periplasmic secretion system and a system for secretion through the outer membrane of the bacterium and a domain for periplasmic localization is a Sec domain or a Tat domain or a signal recognition particle domain. In some embodiments, the polypeptide secretion system includes a periplasmic secretion system and a system for secretion through the outer membrane of the bacterium and a domain for periplasmic localization is a component of a Sec system, a component of a Tat system or a component of a signal recognition particle system. In some embodiments, the polypeptide secretion system includes a periplasmic secretion system and a system for secretion through the outer membrane of the bacterium and wherein the system for secretion through the outer membrane of the bacterium is a N22 system. In some embodiments, the polypeptide secretion system includes a periplasmic secretion system and a system for secretion through the outer membrane of the bacterium and wherein the system for secretion through the outer membrane of the bacterium is a YebF system. In some embodiments, the polypeptide secretion system includes a periplasmic secretion system and a system for secretion through the outer membrane of the bacterium and wherein a domain for directing the recombinant protein to the outer membrane for secretion is an N22 domain or a YebF domain.

In some embodiments, the exogenous nucleic acid further encodes the recombinant protein to include one or more of an amyloid domain, an elastin domain or a collagen domain. In some embodiments, the exogenous nucleic acid further encodes the recombinant protein to include a CsgA domain.

In some embodiments, the bacterium is *E. coli*. In some embodiments, the bacterium is non-pathogenic.

In some embodiments, the silk fibrin domain includes the amino acid sequence GRGGLGGQGAGMAAAAAMG-GAGQGGYGGLGSQGTS (SEQ ID NO: 3). In some embodiments, the silk fibrin domain includes 4 to 64 repeats of the amino acid sequence

```
                                         (SEQ ID NO: 3)
    GRGGLGGQGAGMAAAAAMGGAGQGGYGGLGSQGTS.
```

In some embodiments, the exogenous nucleic acid further encodes the recombinant protein to include one or more functional proteins. In some embodiments, the exogenous nucleic acid further encodes the recombinant protein to include one or more functional proteins comprising an enzyme, an antibody or a detectable protein.

In some embodiments, the recombinant protein is unattached to the bacterium. In some embodiments, the recombinant protein is attached to the bacterium.

In another aspect, provided herein is a genetically-modified bacterium comprising one or more genomic nucleic acids encoding a polypeptide secretion system and further including an exogenous nucleic acid encoding a recombinant protein including a domain for periplasmic localization, a domain for directing the recombinant protein to the outer membrane for secretion and one or more silk fibroin domains, wherein the exogenous nucleic acid is under operation of a promoter to express the recombinant protein.

In some embodiments, the polypeptide secretion system is a Type VIII secretion system or a HlyA Type 1 secretion system. In some embodiments, the polypeptide secretion system includes a periplasmic secretion system and a system for secretion through the outer membrane of the bacterium. In some embodiments, the polypeptide secretion system includes a periplasmic secretion system and a system for secretion through the outer membrane of the bacterium and wherein the periplasmic secretion system is a Sec system. In some embodiments, the polypeptide secretion system includes a periplasmic secretion system and a system for secretion through the outer membrane of the bacterium and wherein the periplasmic secretion system is a twin-arginine translocation (Tat) system. In some embodiments, the polypeptide secretion system includes a periplasmic secretion system and a system for secretion through the outer membrane of the bacterium and wherein the periplasmic secretion system is a signal recognition particle (SRP) system. In some embodiments, the polypeptide secretion system includes a periplasmic secretion system and a system for secretion through the outer membrane of the bacterium and a domain for periplasmic localization is a Sec domain or a Tat domain or a signal recognition particle domain. In some embodiments, the polypeptide secretion system includes a periplasmic secretion system and a system for secretion through the outer membrane of the bacterium and a domain for periplasmic localization is a component of a Sec system, a component of a Tat system or a component of a signal recognition particle system. In some embodiments, In some embodiments, the polypeptide secretion system includes a periplasmic secretion system and a system for secretion through the outer membrane of the bacterium and wherein the system for secretion through the outer membrane of the bacterium is a N22 system. In some embodiments, the polypeptide secretion system includes a periplasmic secretion system and a system for secretion through the outer membrane of the bacterium and wherein the system for secretion through the outer membrane of the bacterium is a YebF system. In some embodiments, the polypeptide secretion system includes a periplasmic secretion system and a system for secretion through the outer membrane of the bacterium and wherein a domain for directing the recombinant protein to the outer membrane for secretion is an N22 domain or a YebF domain.

In some embodiments, the exogenous nucleic acid further encodes the recombinant protein to include one or more of an amyloid domain, an elastin domain or a collagen domain. In some embodiments, the exogenous nucleic acid further encodes the recombinant protein to include a CsgA domain.

In some embodiments, the bacterium is *E. coli*. In some embodiments, the bacterium is non-pathogenic.

In some embodiments, the silk fibrin domain includes the amino acid sequence GRGGLGGQGAGMAAAAAMG-GAGQGGYGGLGSQGTS (SEQ ID NO: 3). In some embodiments, the silk fibrin domain includes 4 to 64 repeats of the amino acid sequence

```
                                         (SEQ ID NO: 3)
    GRGGLGGQGAGMAAAAAMGGAGQGGYGGLGSQGTS.
```

In some embodiments, the exogenous nucleic acid further encodes the recombinant protein to include one or more functional proteins. In some embodiments, the exogenous nucleic acid further encodes the recombinant protein to include one or more functional proteins comprising an enzyme, an antibody or a detectable protein.

In some embodiments, the recombinant protein is unattached to the bacterium. In some embodiments, the recombinant protein is attached to the bacterium.

In another aspect, provided herein is a non-naturally occurring protein including a fusion of a domain for periplasmic localization of the protein to periplasm of a bacterium, a domain for directing the protein to the outer membrane of a bacterium for secretion and one or more silk fibroin domains.

In yet another aspect, provided herein is a nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains.

In another aspect, provided herein is a vector comprising a nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains.

In yet another aspect, provided herein is a bacterium including a foreign or exogenous nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains.

In another aspect, provided herein is a bacterium including a vector comprising a foreign or exogenous nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains.

In yet another aspect, provided herein is a bacterium expressing a foreign or exogenous nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains.

In another aspect, provided herein is a biofilm including a bacterium expressing a foreign or exogenous nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains. In some embodiments, the silk fibroin domains are spider silk fibrin domains which form spider silk.

In one aspect, provided herein is an engineered bacterium comprising a heterologous nucleic acid encoding a recombinant silk protein, wherein the recombinant silk protein comprises a periplasmic translocation signal sequence, an outer membrane secretion signal sequence, and a silk fibroin domain.

In one embodiment, the recombinant silk protein further comprises an amyloid domain, an elastin domain or a collagen domain. In one embodiment, the recombinant silk protein further comprises an amyloid domain. In one embodiment, the amyloid domain comprises CsgA.

In one embodiment, the engineered bacterium comprises a native polypeptide secretion system. In one embodiment, the engineered bacterium further comprises a heterologous nucleic acid encoding a polypeptide secretion system or component of a polypeptide secretion system. In one embodiment, the polypeptide secretion system is a Type VIII secretion system or a HlyA Type 1 secretion system.

In one embodiment, the polypeptide secretion system mediates the transport of a polypeptide from the cytoplasm to the periplasm of the bacterium. In one embodiment, the polypeptide secretion system mediates the secretion of a polypeptide through the outer membrane of the bacterium. In one embodiment, the polypeptide secretion system mediates the transport of a polypeptide from the cytoplasm to the periplasm of the bacterium and through the outer membrane of the bacterium.

In one embodiment, the polypeptide secretion system comprises a Sec system. In one embodiment, the Sec system comprises one or more of SecA, SecB, SecD, SecE, SecF, SecG, SecY, and YajC. In one embodiment, the polypeptide secretion system comprises a twin-arginine translocation (Tat) system. In one embodiment, the Tat system comprises one or more of TatA, TatB, TatE, and TatC. In one embodiment, the polypeptide secretion system is a signal recognition particle (SRP) system. In one embodiment, the SRP system comprises one or more of Ffh, FtsY, and 4.5S RNA.

In one embodiment, the periplasmic translocation signal sequence is a Sec signal sequence, a Tat signal sequence, or a SRP signal sequence. In one embodiment, the periplasmic translocation signal sequence is a Sec signal sequence. In one embodiment, the periplasmic translocation signal sequence is a Tat signal sequence.

In one embodiment, the periplasmic translocation signal sequence is a SRP signal sequence. In one embodiment, the SRP signal sequence comprises the signal sequence of a protein selected from the group consisting of TorT, SfmC, TraU, FocC, TreA, CcmH, FecB, YraI, TolB, AsmA, NikA, FlgI, DsbA, AppA, PcoE, BtuF, PapJ, YbcL, DsbC, ArtJ, ArtI, YraP, YcfS, FlgA, LivK, Agp, ModA, MalE, PhoA, LivJ, FepB, EcoT, MepA, AnsB, and Ivy. In one embodiment, the periplasmic translocation signal sequence comprises an amino acid sequence as set forth in SEQ ID NOs: 10-2029.

In one embodiment, the polypeptide secretion system comprises a curli export system. In one embodiment, the curli export system comprises CsgG. In one embodiment, the curli export system comprises CsgE.

In one embodiment, the polypeptide secretion system comprises a YebF export system. In one embodiment, the YebF export system comprises one or more of OmpC, OmpF and OmpX.

In one embodiment, the outer membrane secretion signal sequence comprises a CsgGE export signal sequence. In one embodiment, the CsgGE export signal sequence comprises the amino acid sequence GVVPQYGGGGNHGGGG-NNSGPN (SEQ ID NO: 2030). In one embodiment, the CsgGE export signal sequence comprises an amino acid sequence as set forth in SEQ ID NOs: 2030-2053.

In one embodiment, the outer membrane secretion signal sequence comprises a YebF signal sequence. In one embodiment, the YebF signal sequence comprises the amino acid sequence MKKRGAFLGLLLVSACASVFA (SEQ ID NO: 668).

In one embodiment, the silk fibroin domain comprises a spider silk fibroin domain. In one embodiment, the silk fibroin domain comprises the amino acid sequence GRG-GLGGQGAGMAAAAAMGGAGQGGYGGLGSQGTS (SEQ ID NO: 3). In one embodiment, the recombinant silk protein comprises 1 to 150 repeats of the silk fibroin domain. In one embodiment, the recombinant silk protein comprises 2 to 64 repeats of the silk fibroin domain.

In one embodiment, the recombinant silk protein comprises a functional protein. In one embodiment, the functional protein is selected from the group consisting of an enzyme, an antibody or a detectable protein. In one embodiment, the detectable protein is selected from the group consisting of a poly-histidine tag, a myc tag, a FLAG tag, a hemagglutinin (HA) tag, and a V5 tag.

In one embodiment, the periplasmic translocation signal sequence and the outer membrane secretion signal sequence are located N-terminal to the silk fibroin domain.

In one embodiment, the heterologous nucleic acid encoding the recombinant silk protein is operably-linked to a promoter. In one embodiment, the promoter is a constitutive promoter. In one embodiment, the promoter is an inducible promoter.

In one embodiment, the bacterium is E. coli. In one embodiment, the bacterium is non-pathogenic.

In one embodiment, the heterologous nucleic acid encoding the recombinant silk protein is located in the bacterial chromosome. In one embodiment, the heterologous nucleic acid encoding the recombinant silk protein is located in a plasmid.

In one aspect, provided herein is a biofilm comprising an engineered bacterium described herein.

In another aspect, provided herein is a method for producing a recombinant silk protein comprising culturing the engineered bacterium described herein under conditions suitable for the expression of the recombinant silk protein in the engineered bacterium.

In one embodiment, the recombinant silk protein is secreted from the engineered bacterium. In one embodiment, the recombinant silk protein forms curli fibers.

In one embodiment, the methods provided herein further comprise collecting the recombinant silk protein from the cell culture medium comprising the engineered bacterium.

In one embodiment, the methods provided herein further comprise purifying the recombinant silk protein.

In another aspect, provided herein is a recombinant silk polypeptide produced using any one of the methods described herein.

In yet another aspect, provided herein is a curli fiber formed from a plurality of recombinant silk proteins, wherein the recombinant silk protein comprise a silk fibroin domain and an amyloid domain. In one embodiment, the amyloid domain comprises CsgA.

In one embodiment, the recombinant silk protein comprises a spider silk fibroin domain. In one embodiment, the silk fibroin domain comprises the amino acid sequence of SEQ ID NO: 3. In one embodiment, the recombinant silk protein comprises 1 to 150 repeats of the silk fibroin domain. In one embodiment, the recombinant silk protein comprises 2 to 64 repeats of the silk fibroin domain.

In one embodiment, the recombinant silk protein comprises an elastin domain or a collagen domain.

In one embodiment, the recombinant silk protein comprises a functional protein. In one embodiment, the functional protein is selected from the group consisting of an enzyme, an antibody or a detectable protein. In one embodiment, the detectable protein is selected from the group consisting of a poly-histidine tag, a myc tag, a FLAG tag, a hemagglutinin (HA) tag, and a V5 tag.

In one aspect, provided herein is a biofilm comprising a curli fiber described herein.

In another aspect, provided herein is a nucleic acid encoding a recombinant silk protein, wherein the recombinant silk protein comprises a periplasmic translocation signal sequence, an outer membrane secretion signal sequence, and a silk fibroin domain.

In one embodiment, the recombinant silk protein further comprises an amyloid domain, an elastin domain or a collagen domain.

In one embodiment, the recombinant silk protein further comprises an amyloid domain. In one embodiment, the amyloid domain comprises CsgA.

In one embodiment, the periplasmic translocation signal sequence is a Sec signal sequence, a Tat signal sequence, or a SRP signal sequence. In one embodiment, the periplasmic translocation signal sequence is a Sec signal sequence. In one embodiment, the periplasmic translocation signal sequence is a Tat signal sequence.

In one embodiment, the periplasmic translocation signal sequence is a SRP signal sequence. In one embodiment, the SRP signal sequence comprises the signal sequence of a protein selected from the group consisting of TorT, SfmC, TraU, FocC, TreA, CcmH, FecB, YraI, TolB, AsmA, NikA, FlgI, DsbA, AppA, PcoE, BtuF, PapJ, YbcL, DsbC, ArtJ, ArtI, YraP, YcfS, FlgA, LivK, Agp, ModA, MalE, PhoA, LivJ, FepB, EcoT, MepA, AnsB, and Ivy.

In one embodiment, the periplasmic translocation signal sequence comprises an amino acid sequence as set forth in SEQ ID NOs: 10-2029.

In one embodiment, the outer membrane secretion signal sequence comprises a CsgGE export signal sequence. In one embodiment, the CsgGE export signal sequence comprises the amino acid sequence GVVPQYGGGGNHGGGG-NNSGPN (SEQ ID NO: 2030). In one embodiment, the CsgGE export signal sequence comprises an amino acid sequence as set forth in SEQ ID NOs: 2030-2053.

In one embodiment, the outer membrane secretion signal sequence comprises a YebF signal sequence. In one embodiment, the YebF signal sequence comprises the amino acid sequence MKKRGAFLGLLLVSACASVFA(SEQ ID NO: 668).

In one embodiment, the silk fibroin domain comprises a spider silk fibroin domain. In one embodiment, the silk fibroin domain comprises the sequence of SEQ ID NO: 3.

In one embodiment, the recombinant silk protein comprises 1 to 150 repeats of the silk fibroin domain. In one embodiment, the recombinant silk protein comprises 2 to 64 repeats of the silk fibroin domain.

In one embodiment, the recombinant silk protein comprises a functional protein. In one embodiment, the functional protein is selected from the group consisting of an enzyme, an antibody or a detectable protein. In one embodiment, the detectable protein is selected from the group consisting of a poly-histidine tag, a myc tag, a FLAG tag, a hemagglutinin (HA) tag, and a V5 tag.

In one embodiment, the periplasmic translocation signal sequence and the outer membrane secretion signal sequence are located N-terminal to the silk fibroin domain.

In one aspect, provided herein is a vector comprising a nucleic acid described herein. In one embodiment, the nucleic acid is operably-linked to a promoter. In one embodiment, the promoter is a constitutive promoter. In one embodiment, the promoter is an inducible promoter.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 3A and FIG. 3B schematically depict Sec-N22 secretion tag silk constructs and Sec-N22 amyloid-silk fusion constructs. The silk domain is a repetitive sequence constructed from the Golden Silk Orb-weaving spider *Nephila clavipes*, (SEQ ID NO: 3)
GRGGLGGQGAGMAAAAAMGGAGQGGYGGLGSQGTS.

DETAILED DESCRIPTION

Figure 1:
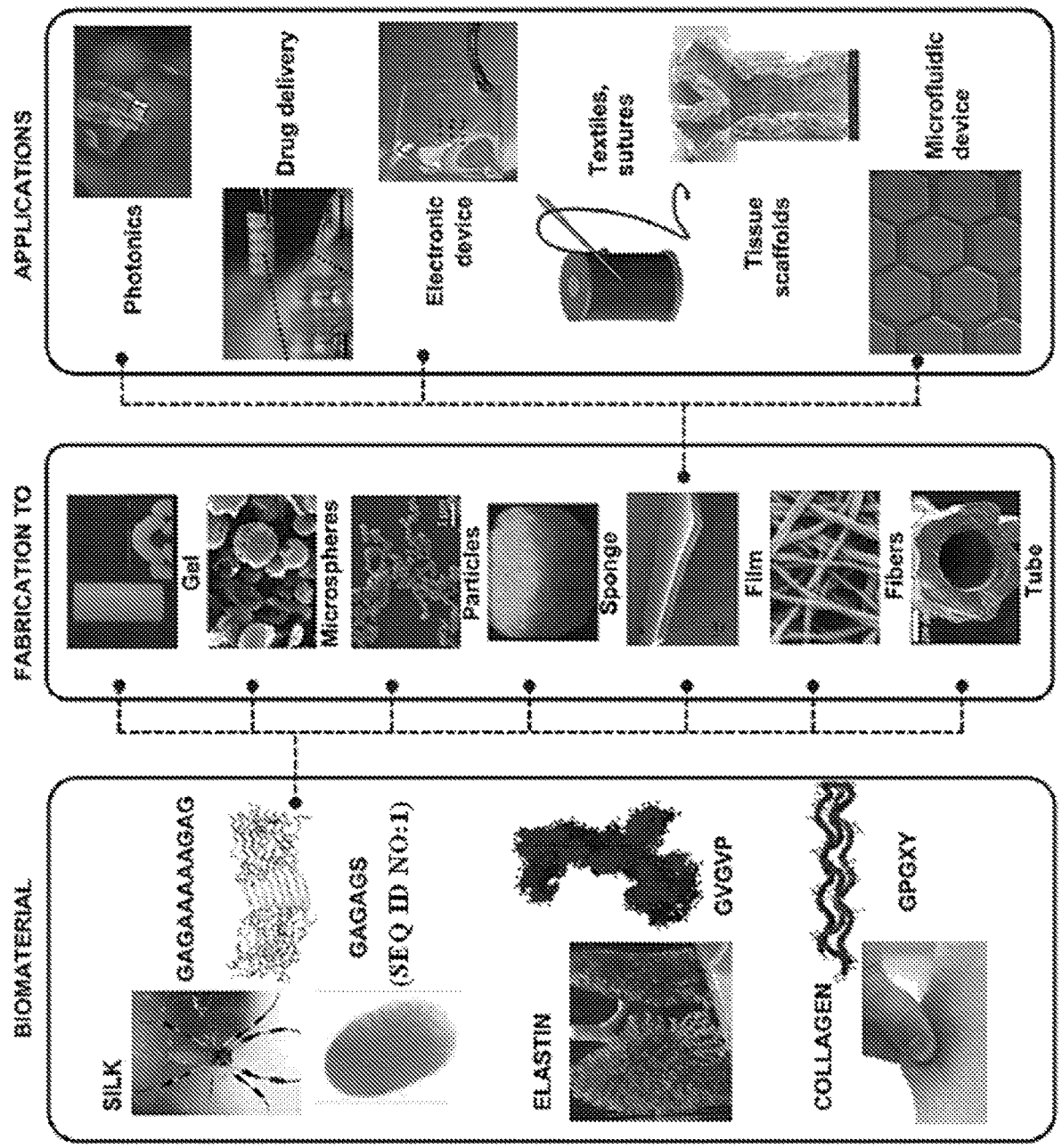
FIG. 1 schematically depicts biomaterials which may be secreted from bacteria according to methods described herein, various fabrication forms and uses.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

As used herein, the term "engineered bacterium" or "engineered bacterial cell" refers to a bacterial cell that has been genetically modified from its native state. For instance, an engineered bacterial cell may have nucleotide insertions, nucleotide deletions, nucleotide rearrangements, and nucleotide modifications introduced into their DNA. These genetic modifications may be present in the chromosome of the bacteria or bacterial cell, or on a plasmid in the bacteria or bacterial cell. Engineered bacterial cells of the disclosure may comprise exogenous nucleotide sequences on plasmids. Alternatively, recombinant bacterial cells may comprise exogenous nucleotide sequences stably incorporated into their chromosome. In some embodiments, the engineered bacterium is non-pathogenic. In some embodiments, the engineered bacterium is pathogenic.

As used herein, the term "gene" refers to a nucleic acid fragment that encodes a protein or fragment thereof, optionally including regulatory sequences preceding (5' non-coding sequences) and following (3' non-coding sequences) the coding sequence. In one embodiment, a "gene" does not include regulatory sequences preceding and following the coding sequence.

As used herein, a "heterologous" gene, "heterologous sequence", or "heterologous nucleic acid" refers to a nucleic acid sequence that is not normally found in a given cell in nature. As used herein, a heterologous sequence encompasses a nucleic acid sequence that is exogenously introduced into a given cell. "Heterologous gene" includes a native gene, or fragment thereof, that has been introduced into the host cell in a form that is different from the corresponding native gene. A heterologous gene may include a native gene, or fragment thereof, introduced into a non-native host cell. Thus, a heterologous gene may be foreign or native to the recipient cell; a nucleic acid sequence that is naturally found in a given cell but expresses an unnatural amount of the nucleic acid and/or the polypeptide which it encodes; and/or two or more nucleic acid sequences that are not found in the same relationship to each other in nature.

As used herein, a "periplasmic translocation signal sequence", refers to a polypeptide sequence which, when present on a polypeptide, e.g., at the N-terminus of a polypeptide, can cause the polypeptide to be exported from the cytoplasm of a bacterium across the inner membrane. In some embodiments, the periplasmic translocation signal sequence facilitates transport (e.g., export) to the bacterial periplasm as mediated by a bacterial Sec system. In some embodiments, the periplasmic translocation signal sequence facilitates transport (e.g., export) to the bacterial periplasm as mediated by a bacterial twin-arginine translocation (Tat) system. In some embodiments, the periplasmic translocation signal sequence facilitates transport (e.g., export) to the bacterial periplasm as mediated by a bacterial signal recognition particle (SRP) system. In some embodiments, the periplasmic translocation signal sequence is a Sec signal sequence, a Tat signal sequence or a SRP signal sequence and homologs and/or variants, including conservative substitution variants, thereof. In some embodiments, the Sec signal sequence comprises a polypeptide having the sequence of *E. coli* CsgA SecA-dependent secretion signal and homologs and/or variants, including conservative substitution variants, thereof. Periplasmic translocation signal sequnces include, but are not limited to, SEQ ID NOs: 10-2029, as disclosed herein. In some embodiments, the periplasmic translocation signal sequence comprises an amino acid sequence having at least 80% homology (e.g., 80% or greater homology, 90% or greater homology, or 95% or greater homology), to the amino acid sequence of a periplasmic translocation signal sequence provided herein e.g. naturally occurring mutations or variants, homologs, or engineered mutations or variants. In some embodiments, the periplasmic translocation signal sequence comprises an amino acid sequence having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of a periplasmic translocation signal sequence provided herein.

As used herein, a "signal recognition particle (SRP) pathway signal sequence" or "SRP signal sequence" refers to a polypeptide sequence which, when present on a polypeptide (e.g., the N-terminus of a polypeptide), can mediate the polypeptide export from the cytoplasm of a bacterium to the periplasmic inner membrane as mediated by the single recognition particle (SRP) pathway proteins. In some embodiments, the polypeptide is translated and transported across the inner membrane concurrently, thus guiding the nascent polypeptide into the periplasm. In some embodiments, the SRP pathway signal sequence is the SRP signal sequence from TorT, SfmC, TraU, FocC, TreA, CcmH, FecB, YraI, TolB, AsmA, NikA, FlgI, DsbA, AppA, PcoE, BtuF, PapJ, YbcL, DsbC, ArtJ, ArtI, YraP, YcfS, FlgA, LivK, Agp, ModA, MalE, PhoA, LivJ, FepB, EcoT, MepA, AnsB, and Ivy, or homologs and/or variants, including conservative substitution variants, thereof. In some embodiments, the SRP signal sequence comprises an amino acid sequence having at least 80% homology (e.g., 80% or greater homology, 90% or greater homology, or 95% or greater homology), to the amino acid sequence of a SRP signal sequence provided herein e.g. naturally occurring mutations or variants, homologs, or engineered mutations or variants. In some embodiments, the SRP signal sequence comprises an amino acid sequence having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of a SRP signal sequence provided herein.

As used herein, an "outer membrane secretion signal sequence" refers to a polypeptide sequence which, when present on a polypeptide can cause the polypeptide to be transported across the outer membrane of a bacterial cell (e.g., a Gram-negative bacterial cell). In some embodiments, the outer membrane secretion signal sequence is a CsgGE export signal sequence. In some embodiments, the outer membrane secretion signal sequence is a YebF signal sequence. In some embodiments, the outer membrane secretion signal sequence comprises an amino acid sequence as set forth in the sequence listing. In some embodiments, the outer membrane secretion signal sequence comprises an amino acid sequence having at least 80% homology (e.g., 80% or greater homology, 90% or greater homology, or 95% or greater homology), to the amino acid sequence of an outer membrane secretion signal sequence provided herein e.g. naturally occurring mutations or variants, homologs, or engineered mutations or variants. In some embodiments, the outer membrane secretion signal sequence comprises an amino acid sequence having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of an outer membrane secretion signal sequence provided herein.

As used herein, a "CsgGE export signal sequence" refers to a polypeptide sequence which, when present on a polypeptide can cause the polypeptide to be targeted by CsgE and exported across the outer membrane of the cell via the CsgG oligomeric transport complex of a curli export system, or by an orthologous export system. In some embodiments, the CsgGE export signal sequence comprises the last 22 amino acids of the bipartite curli signal sequence of an endogenous polypeptide exported by the curli export system. In some embodiments, the CsgGE export signal sequence comprises be a polypeptide having the sequence of an E. coli CsgA CsgGE export signal sequence (e.g., GVVPQYGGGGNHGGGGNNSGPN; SEQ ID NO: 2030; also referred to herein as N22 domain) and homologs and/or variants, including conservative substitution variants, thereof. In some embodiments, the CsgGE export signal sequence comprises an amino acid sequence as set forth in SEQ ID NOs: 2030-2053. In some embodiments, the CsgGE export signal sequence comprises an amino acid sequence having at least 80% homology (e.g., 80% or greater homology, 90% or greater homology, or 95% or greater homology), to the amino acid sequence of a CsgGE export signal sequence provided herein e.g. naturally occurring mutations or variants, homologs, or engineered mutations or variants. In some embodiments, the CsgGE export signal sequence comprise an amino acid sequence having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of a CsgGE export signal sequence provided herein.

A "polypeptide secretion system", as used herein, refers to one or more proteins, nucleic acids, and/or cofactors that mediate the export of a polypeptide from the cytoplasm of a bacterial cell (e.g., through the inner membrane, to the periplasm, through the outer membrane, to the cell surface and/or to the extracellular milieu of a bacterial cell). In some embodiments, the bacterial cell is a Gram-negative bacterial cell. In some embodiments, the bacterial cell is a Gram-positive bacterial cell.

A "promoter" as used herein, refers to a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell-specific or tissue-specific manner, in response to different environmental or physiological conditions, or in response to specific compounds. Prokaryotic promoters are typically classified into two classes: inducible and constitutive.

"Constitutive promoter" refers to a promoter that is capable of facilitating continuous transcription of a coding sequence or gene under its control and/or to which it is operably linked. Constitutive promoters and variants are well known in the art and include, but are not limited to, a constitutive Escherichia coli σS promoter, a constitutive Escherichia coli σ32 promoter, a constitutive Escherichia coli σ70 promoter, a constitutive Bacillus subtilis σA promoter, a constitutive Bacillus subtilis σB promoter, and a bacteriophage T7 promoter.

An "inducible promoter" refers to a promoter that initiates increased levels of transcription of the coding sequence or gene under its control in response to a stimulus or an exogenous environmental condition. A "directly inducible promoter" refers to a regulatory region, wherein the regulatory region is operably linked to a gene encoding a protein or polypeptide, where, in the presence of an inducer of said regulatory region, the protein or polypeptide is expressed. An "indirectly inducible promoter" refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by "inducible promoter." As used herein, the term "expression" refers to the transcription and stable accumulation of sense (mRNA) or anti-sense RNA derived from a nucleic acid, and/or to translation of an mRNA into a polypeptide The term "genetic modification," as used herein, refers to any genetic change. Exemplary genetic modifications include those that increase, decrease, or abolish the expression of a gene, including, for example, modifications of native chromosomal or extrachromosomal genetic material. Exemplary genetic modifications also include the introduction of at least one plasmid, modification, mutation, base deletion, base addition, and/or codon modification of chromosomal or extrachromosomal genetic sequence(s), gene over-expression, gene amplification, gene suppression, promoter modification or substitution, gene addition (either single or multi-copy), antisense expression or suppression, or any other change to the genetic elements of a host cell, whether the change produces a change in phenotype or not. Genetic modification can include the introduction of a plasmid, e.g., a plasmid comprising at least one amino acid catabolism enzyme operably linked to a promoter, into a bacterial cell. Genetic modification can also involve a targeted replacement in the chromosome, e.g., to replace a native gene promoter with an inducible promoter, regulated promoter, strong promoter, or constitutive promoter. Genetic modification can also involve gene amplification, e.g., introduction of at least one additional copy of a native gene into the chromosome of the cell. Alternatively, chromosomal genetic modification can involve a genetic mutation.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

As used herein, the term "exogenous" refers to a substance (e.g., a nucleic acid or polypeptide) present in a cell other than its native source. The term exogenous can refer to a nucleic acid or a protein that has been introduced by a process involving the hand of man into a biological system such as a cell or organism in which it is not normally found or in which it is found in undetectable amounts. A substance can be considered exogenous if it is introduced into a cell or an ancestor of the cell that inherits the substance. In contrast, the term "endogenous" or "native" refers to a substance that is naturally-present in the biological system or cell.

A "plasmid" or "vector" includes a nucleic acid construct designed for delivery to a host cell or transfer between different host cell. An "expression plasmid" or "expression vector" can be a plasmid that has the ability to incorporate and express heterologous nucleic acid fragments in a cell. An expression plasmid may comprise additional elements, for example, the expression vector may have two replication systems, thus allowing it to be maintained in two organisms. The nucleic acid incorporated into the plasmid can be operatively linked to an expression control sequence when the expression control sequence controls and regulates the transcription and translation of that polynucleotide sequence.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. The terms "protein" and "polypeptide" as used herein refer to both large polypeptides and small peptides. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

The term "operatively linked" includes having an appropriate transcription start signal (e.g., promoter) in front of the polynucleotide sequence to be expressed, and having an appropriate translation start signal (e.g., a Shine Delgarno sequence and a start codon (ATG)) in front of the polypeptide coding sequence and maintaining the correct reading frame to permit expression of the polynucleotide sequence under the control of the expression control sequence, and, optionally, production of the desired polypeptide encoded by the polynucleotide sequence. In some examples, transcription of a gene encoding a recombinant polypeptide as described herein is under the control of a promoter sequence (or other transcriptional regulatory sequence) which controls the expression of the nucleic acid in a cell-type in which expression is intended. It will also be understood that the gene encoding a recombinant polypeptide as described herein can be under the control of transcriptional regulatory sequences which are the same or which are different from those sequences which control transcription of the naturally-occurring form of a protein.

The terms "overexpression" or "overexpress", as used herein refers to the expression of a functional nucleic acid, polypeptide or protein encoded by DNA in a host cell, wherein the nucleic acid, polypeptide or protein is either not normally present in the host cell, or wherein the nucleic acid, polypeptide or protein is present in the host cell at a higher level than that normally expressed from the endogenous gene encoding the nucleic acid, polypeptide or protein.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "non-pathogenic" as used herein to refer to bacteria refers to bacteria that are not capable of causing disease or harmful responses in a host. In some embodiments, non-pathogenic bacteria are commensal bacteria. Naturally pathogenic bacteria may be genetically engineered to provide reduce or eliminate pathogenicity.

With respect to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure. A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, polypeptide described herein can be a variant of a sequence described herein, e.g., a conservative substitution variant of a polypeptide comprising the amino acid sequence of SEQ ID NO: 1. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity, e.g. ability to target a polypeptide for export via the curli export system. A wide variety of PCR-based site-specific mutagenesis approaches are also known in the art and can be applied by the ordinarily skilled artisan.

A variant amino acid or DNA sequence can be at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

Other than in the operating examples, or where otherwise indicated, all numbers expressing quantities of ingredients or reaction conditions used herein should be understood as modified in all instances by the term "about." The term "about" when used in connection with percentages can mean ±1%.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In one aspect, the present disclosure is directed to the use of a secretion system in a bacterium to secrete a non-native polypeptide from the bacterium and into the surrounding environment. The bacterium may be genetically-altered to include a heterologous encoding the nonnative polypeptide. In some embodiments, the non-native polypeptide is expressed and secreted from the bacterium using a bacterial secretion system which may be native to the bacterium or non-native to the bacterium. A bacterial secretion system which is nonnative to the bacterium is one which has been introduced into the bacterium, for example, through genetic modification of the bacterium to include nucleic acids encoding the non-native or foreign secretion system or components of a non-native secretion system. In some embodiments, the non-native polypeptide is expressed by the bacterium but not secreted from the bacterium.

In one aspect, the present invention provides an engineered bacterium comprising a heterologous nucleic acid encoding a recombinant silk protein, wherein the recombinant silk protein comprises a periplasmic translocation signal sequence, an outer membrane secretion signal sequence, and a silk fibroin domain. Without wishing to be bound by any particular theory, the expression of the recombinant silk proteins comprising said signal sequence provides for the robust production and secretion of silk proteins which may be readily purified and used for multiple applications.

In some embodiments, the heterologous nucleic acid encoding a recombinant silk protein comprises a heterologous nucleic acid encoding a periplasmic translocation signal sequence. In some embodiments, the periplasmic translocation signal sequence facilitates the export of the recombinant silk polypeptide from the cytoplasm of the bacterium to the periplasm of the bacterium via an endogenous or heterologous polypeptide secretion system. In some embodiments, the heterologous nucleic acid encoding a recombinant silk protein comprises multiple heterologous nucleic acid sequences encoding a periplasmic translocation signal sequence (e.g., one, two, three, four, five, or six nucleic acid sequences encoding a periplasmic translocation signal sequence). In some embodiments, the polypeptide secretion system that mediates the secretion of the polypeptide from the cytoplasm to the periplasmic space of the bacterium is a Sec system, a twin-arginine translocation (Tat) system, or a signal recognition particle (SRP) system. In some embodiments, the heterologous nucleic acid encoding recombinant silk protein encodes a periplasmic translocation signal sequence selected from the group consisting of a Sec signal sequence, a Tat signal sequence, and a SRP signal sequence. In some embodiments, the recombinant silk protein comprises a periplasmic translocation signal sequence. In some embodiments, the recombinant silk protein comprises a periplasmic translocation signal sequence selected from the group consisting of a Sec signal sequence, a Tat signal sequence, and a SRP signal sequence. In some embodiments, the recombinant silk protein comprises multiple periplasmic translocation signal sequences (e.g., one, two, three, four, five, or six periplasmic translocation signal sequences). In some embodiments, the periplasmic translocation sequence is N-terminal of the polypeptide. In some embodiments, the periplasmic translocation signal sequence is N-terminal of the outer membrane secretion signal sequence. In some embodiments, the periplasmic translocation sequence is C-terminal of the outer membrane secretion signal sequence. Other polypeptide secretion systems that mediate the transport (e.g., export) of polypeptides from the cytoplasm to the periplasmic space of the bacterium and their cognate signal peptides are known in the art and may be used as described herein (see, e.g., Green and Mecsas (2016) *Microbiol. Spectr.* 4:1; doi: 10.1128/microbiolspec.VMBF-0012-2015, the contents of which are incorporated herein by reference).

Bacterial secretion systems may be used to secrete a silk protein described herein (e.g., a silk protein comprising a silk fibroin domain) through a heterologous system evolved for the secretion of other proteins. Such secretions systems are known to those of skill in the art and include, for example: 1) systems for periplasmic secretion, and 2) systems for secretion from the periplasm, across the outer membrane, and into the extracellular milieu. An exemplary system for periplasmic secretion includes a Twin-arginine Translocation (Tat) system which exports fully folded proteins to the periplasm (see, e.g., Lee PA, Tullman-Ercek D, Georgiou G, "The bacterial twin-arginine translocation pathway", *Annu Rev Microbiol.* 60:373-95 (2006) PMID: 16756481, which is hereby incorporated by reference in its entirety). An exemplary system for periplasmic secretion includes a Signal Recognition Particle (SRP) system which mediates co-translational secretion into the periplasm (see. e.g., Saraogi I, Shan SO, "Co-translational protein targeting to the bacterial membrane", *Biochim. Biophys. Acta.* 1843 (8): 1433-41 (2014) doi: 10.1016/j.bbamcr.2013.10.013, PMID: 24513458, which is hereby incorporated by reference in its entirety).

The Sec system, also known as the Sec secretion pathway, primarily translocates proteins to the periplasmic space in their unfolded state (see, e.g., Beckwith (2013) *Res. Microbiol.* 164(6): 497-504). The Sec system consists of a protein targeting component, a motor protein and a membrane-integrated channel, called the SecYEG translocase complex, which is stably formed by the SecY, SecE and SecG proteins (encoded by the secY, secE and secG genes, respectively). SecB (encoded by the secB gene) is a chaperone protein that interacts with the nascent chain of the proteins preventing their folding. SecA (encoded by the secA gene) is an ATPase that interacts with SecB as well as the SecYEG translocase complex. Proteins not requiring SecB to prevent folding may be recognized by SecA and transferred during synthesis to the SecYEG translocase complex. SecA remains bound to SecYEG translocase complex as the protein is translocated and is released when the export is complete. Additional proteins that may be involved in the Sec system-mediated export of proteins from the cytoplasm to the periplasmic space include SecD and SecF (encoded by the secD and secF genes, respectively), which form the SecDF complex and may function as chaperone proteins, and YajC (encoded by the yajC gene) which co-purifies with the SecDF complex. The function of YajC is unclear.

In some embodiments, the bacterium comprises an endogenous Sec system. In some embodiments, the bacterium comprises an endogenous secY gene. In some embodiments, the bacterium comprises an endogenous secE gene. In some embodiments, the bacterium comprises an endogenous secG gene. In some embodiments, the bacterium comprises an endogenous secB gene. In some embodiments, the bacterium comprises an endogenous secA gene. In some embodiments, the bacterium comprises an endogenous secD gene. In some embodiments, the bacterium comprises an endogenous secF gene. In some embodiments, the bacterium comprises an endogenous yajC gene.

In some embodiments, the bacterium has been genetically-modified to comprise a heterologous Sec system. In some embodiments, the bacterium has been genetically-modified to comprise a heterologous secY gene. In some embodiments, the bacterium has been genetically-modified to comprise a heterologous secE gene. In some embodiments, the bacterium has been genetically-modified to comprise a heterologous secG gene. In some embodiments, the bacterium has been genetically-modified to comprise a heterologous secB gene. In some embodiments, the bacterium has been genetically-modified to comprise a heterologous secA gene. In some embodiments, the bacterium has been genetically-modified to comprise a heterologous secD gene. In some embodiments, the bacterium has been genetically-modified to comprise a heterologous secF gene. In some embodiments, the bacterium has been genetically-modified to comprise a heterologous yajC gene. In some embodiments, the bacterium has been genetically-modified to comprise one or more of a heterologous secY gene, a heterologous secE gene, a heterologous secG gene, a heterologous secB gene, a heterologous secA gene, a heterologous secD gene, a heterologous secF gene, and a heterologous yajC gene.

The twin arginine Tat system, also known as the Tat pathway, mediates the translocation of folded proteins across lipid bilayers, for example, from the cytoplasm to the periplasmic space (see, e.g., Robinson et al. (2011) *Biochimica et Biophysica Acta* 1808: 876-884; and Goosens et al. (2014) *Biochimica et Biophysica Acta* 1843: 1698-1706. Tat systems are present in both Gram-negative and Gram-positive bacteria. In *E. coli*, the Tat system is comprised of TatA, TatB and TatC subunits which mediate protein translocation, and are encoded by tatA, tatB and tatC genes. In *E coli*, an additional subunit TatE, encoded by the tatE gene partially complements tatA null mutants and appears to be redundant.

In some embodiments, the bacterium comprises an endogenous Tat system. In some embodiments, the bacterium comprises an endogenous tatA gene. In some embodiments, the bacterium comprises an endogenous tatB gene. In some embodiments, the bacterium comprises an endogenous tatC gene. In some embodiments, the bacterium comprises an endogenous tatE gene. In some embodiments, the bacterium comprises an endogenous tatABC operon.

In some embodiments, the bacterium has been genetically-modified to comprise a heterologous Tat system. In some embodiments, the bacterium has been genetically-modified to comprise a heterologous tatA gene. In some embodiments, the bacterium has been genetically-modified to comprise a heterologous tatB gene. In some embodiments, the bacterium has been genetically-modified to comprise a heterologous tatC gene. In some embodiments, the bacterium has been genetically-modified to comprise a heterologous tatE gene. In some embodiments, the bacterium has been genetically-modified to comprise a heterologous tatABC operon. In some embodiments, the bacterium has been genetically-modified to comprise one or more of a heterologous tatA gene, a heterologous tatB gene, a heterologous tatC gene, a heterologous tatE gene, and a heterologous tatABC operon.

The SRP pathway is a polypeptide transport system in bacterial cells which mediates the co-translational translocation of proteins through the inner membrane and into the periplasm. In the SRP system, a specific N-terminal protein sequence is recognized by a complex comprising, Ffh protein and a 4.5S RNA, which guides the nascent polypeptide chain directly into the periplasm via the FtsY receptor. In some embodiments, the SRP pathway signal sequence is cleavable (see, e.g., Schierle et al. (2003) J. Bacteriol. 185(19): 5706-13). Any known SRP pathway signal sequences can be used as described herein.

In some embodiments, the bacterium has been genetically-modified to comprise a heterologous ffh gene (which encodes Ffh protein). In some embodiments, the bacterium has been genetically-modified to comprise a heterologous ftsY gene (which encodes the signal recognition particle receptor protein FtsY). In some embodiments, the bacterium has been genetically engineered to comprise a heterologous ffs gene (which encodes 4.5S RNA). In some embodiments, the bacterium has been genetically-modified to comprise one or more of a heterologous ffh gene, a heterologous ftsY gene, and a heterologous ffs gene.

In some embodiments, the recombinant silk protein comprises a SRP signal sequence. In some embodiments, the heterologous nucleic acid encoding the recombinant silk protein comprises a SRP signal sequence selected from the group consisting of the SRP signal sequence comprises the signal sequence of a protein selected from the group consisting of TorT, SfmC, TraU, FocC, TreA, CcmH, FecB, YraI, TolB, AsmA, NikA, FlgI, DsbA, AppA, PcoE, BtuF, PapJ, YbcL, DsbC, ArtJ, ArtI, YraP, YcfS, FlgA, LivK, Agp, ModA, MalE, PhoA, LivJ, FepB, EcoT, MepA, AnsB, and Ivy, or homologs and/or variants, including conservative substitution variants, thereof.

In some embodiments, the recombinant silk protein comprises a periplasmic translocation signal sequence comprising an amino acid sequence as set forth in the sequence listing, or homologs and/or variants, including conservative substitution variants, thereof. In some embodiments, the heterologous nucleic acid encoding the recombinant silk protein comprises a periplasmic translocation signal sequence comprising an amino acid sequence as set forth in the sequence listing, or homologs and/or variants, including conservative substitution variants, thereof.

In some embodiments, the heterologous nucleic acid encoding the recombinant silk protein comprises a heterologous nucleic acid encoding an outer membrane secretion signal sequence. In some embodiments, the heterologous nucleic acid encoding a recombinant silk protein comprises multiple heterologous nucleic acid sequences encoding an outer membrane secretion signal sequence (e.g., one, two, three, four, five, or six nucleic acid sequences encoding an outer membrane secretion signal sequence). In some embodiments, the recombinant silk protein comprises an outer membrane secretion signal sequence. In some embodiments, the recombinant silk protein comprises multiple outer membrane secretion signal sequences (e.g., one, two, three, four, five, or six outer membrane secretion signal sequence).

In some embodiments, the outer membrane secretion signal sequence is N-terminal of the outer membrane secretion signal sequence. In some embodiments, the outer membrane secretion signal sequence is C-terminal of the periplasmic translocation signal sequence. The outer membrane signal sequence mediates the secretion of the protein through the outer membrane of the bacterium.

In some embodiments, the outer membrane signal sequence mediates the transport of the protein via a curli export system. In some embodiments, the outer membrane export signal sequence is a CsgGE export signal sequence, or homologs and/or variants, including conservative substitution variants, thereof. In some embodiments, the heterologous nucleic acid encoding the recombinant silk protein comprises a heterologous nucleic acid encoding a CsgGE export signal sequence, or homologs and/or variants, including conservative substitution variants, thereof. In some embodiments, the recombinant silk protein comprises a CsgGE export signal sequence, or homologs and/or variants, including conservative substitution variants, thereof. The CsgGE export signal sequence facilitates the transport of a polypeptide comprising the CsgGE export signal sequence from the bacterial periplasm via a bacterial type-8 secretion system. The Type-8 Secretion System (T8SS) of Gram-negative bacteria, such as *Escherichia coli*, is a dedicated protein export system that has evolved for the secretion of functional amyloids (e.g., an amyloid polypeptide) to the extracellular space. These amyloids then self-assemble to form nanofibers implicated in pathogenesis of epithelial tissue and biofilm persistence (Chapman et al. (2002) Science 295(5556): 851-855). The outer membrane porin for the T8SS is composed of nonameric outer membrane protein, CsgG. The fully assembled CsgG complex contains a 2 nm transmembrane channel (Goyal et al. (2014) Nature 516: 250-3). The structural monomeric unit of the functional amyloid, CsgA, is exported to the extracellular space via CsgG through a specific CsgG-specific N-terminal peptide tag, called N22. This event is preceded by translocation of the cytoplasmically-expressed CsgA protein to the periplasm through the Sec system, the major periplasmic export system in bacteria. An additional periplasmically-localized protein, CsgE, confers N22-containing substrate specificity for CsgG export and forms a multimeric complex with CsgG, encapsulating the protein to be exported and creating an entropic free-energy gradient that is thought to drive the export through the CsgG channel. In the absence of CsgE, the CsgG porin is ungated, allowing for passive diffusion of molecules through the outer membrane (Nenninger et al. (2011) Molecular Microbiology 81(2): 486-499).

In some embodiments, the CsgGE export signal sequence is an *E. coli* CsgGE export signal sequence. In some embodiments, the *E. coli* CsgGE export signal sequence comprises the amino acid sequence GVVPQYGGGG-NHGGGGNNSGPN (SEQ ID NO: 2030; referred to herein as N22).

Any CsgGE export signal sequence known in the art and homologs and/or variants, including conservative substitution variants, may be used as described herein. In some embodiments, the CsgGE export signal sequence comprises an amino acid sequence as set forth in the sequence listing, or homologs and/or variants, including conservative substitution variants, thereof. In some embodiments, the CsgGE export signal sequences comprises an amino acid sequence selected from the group consisting of GVVPQYGGGG-NHGGGGNNSGPN (SEQ ID NO: 2030), GVVPQWGGGGNHNGGGNSSGPD (SEQ ID NO: 2031), GVVPQYGGGNHGGGNGGGSNNSGPN (SEQ ID NO: 2032), GVVPQYGGGGNHGGGGN (SEQ ID NO: 2033), IPQYGGGNHGGGGNNSGPN (SEQ ID NO: 2034), IPQFGGGGHHGGGGNNSGPN (SEQ ID NO: 2035), GVVPQWGGGGNHNGGGNNSGPD (SEQ ID NO: 2036), IPQYGGGGGNHGGGGNNSGPN (SEQ ID NO: 2037), GAIPQYGGGGGGNHGGGGNNSGPN (SEQ ID NO: 2038), IPQYGGGGNHGGGGNNSGPN (SEQ ID NO: 2039), GVVPQYGGGNHGGGGNNSGPN (SEQ ID NO: 2040), GVVPQYGGGGNLGGGGNNSGPN (SEQ ID NO: 2041), GVVPQYGGGGNYGGGGNNSGPN (SEQ ID NO: 2042), GAVPQFGGGHGGGWGGGNNGPD (SEQ ID NO: 2043), GAIPQYGHGGGWGGGNSGPN (SEQ ID NO: 2044), IPQYGGGHGGGSNNGP (SEQ ID NO: 2045), GAVPQFGGHGHGHGGGGNSGPD (SEQ ID NO: 2046), GLVPQYGGGHGGGNTTGP (SEQ ID NO: 2047), GVVPQWGGNHHGGGNNYGPD (SEQ ID NO: 2048), GVVPQWGGSGHHNGGNNNGPD (SEQ ID NO: 2049), VPQYGNGGGHGGGSNGPN (SEQ ID NO: 2050), GLVPQYGGGHGGGGSTTGP (SEQ ID NO: 2051), VPQYGHGGNGGWGGNNGGPN (SEQ ID NO: 2052), GTVPQFGGGGGHNPGNGNNNGPN (SEQ ID NO: 2053), or homologs and/or variants, including conservative substitution variants, thereof. In addition, any export signal sequence that mediates the export of a polypeptide to the extracellular milieu that is orthologous to a curli export system may be used as described herein.

In some embodiments, the bacterium has been genetically-modified to comprise a heterologous csgE gene (which encodes CsgE). In some embodiments, the heterologous csgE gene is an *E. coli* csgE gene. In some embodiments, the bacterium has been genetically-engineered to comprise a heterologous csgG gene. In some embodiments, the heterologous csgE gene is an *E. coli* csgG gene (which encodes CsgG). In some embodiments, the bacterium has been genetically-modified to comprise a heterologous csgE gene and a heterologous csgG gene.

In some embodiments, the outer membrane signal sequence mediates the transport of the protein via a YebF export system. In some embodiments, the heterologous nucleic acid encoding the recombinant silk protein comprises a heterologous nucleic acid encoding a YebF signal sequence, or homologs and/or variants, including conservative substitution variants, thereof. In some embodiments, the recombinant silk protein comprises a YebF signal sequence, or homologs and/or variants, including conservative substitution variants, thereof. In some embodiments, the YebF signal sequence comprises the amino acid sequence as set forth in the sequence listing, or homologs and/or variants, including conservative substitution variants, thereof. The YebF export system mediates the secretion of a protein of interest by fusion to the YebF protein, which is secreted by *E. coli* (see, e.g., Zhang et al. (2006) *Nat. Biotechnol.* 24(1): 100-4; and Prehna et al. (2012) *Structure* 20(7): 1154-66, the contents of each which are hereby incorporated by reference in their entirety). The outer membrane proteins OmpC, OmpF, and OmpX (encoded by the ompC, ompF and ompX genes, respectively) mediate the outer membrane export of the YebF protein.

In some embodiments, the bacterium has been genetically-modified to comprise a heterologous ompC gene. In some embodiments, the bacterium has been genetically-engineered to comprise a heterologous ompF gene. In some embodiments, the bacterium has been genetically-modified to comprise a heterologous ompX gene. In some embodiments, the bacterium has been genetically-modified to comprise one or more of a heterologous ompC gene, a heterologous ompF gene, and a heterologous ompX gene.

Other exemplary system for secretion through the outer membrane includes the HlyA Type 1 secretion system (T1SS), which mediates secretion from the cytoplasm directly into the extracellular space via the hemolysin export system (see, e.g., Thomas et al., "The Type 1 secretion pathway—the hemolysin system and beyond", *Biochim Biophys Acta* 1843(8): 1629-41 (2014), doi:10.1016/j.bbamcr.2013.09.017, PMID:24129268, which is hereby incorporated by reference in its entirety).

In some embodiments, the heterologous nucleic acid encoding the recombinant silk protein comprises a heterologous nucleic acid encoding a silk fibroin domain. In some embodiments, the recombinant silk protein comprises a silk fibroin domain. A nonnative polypeptide within the scope of the present disclosure is spider silk. In some embodiments, the silk fibroin domain is a spider silk fibroin domain. Spider silk is composed of two major fibroin proteins, or 'spidroins', which are repetitive modular proteins of high molecular weight. The primary structure of the spidroin consists of ordered amino- and carboxy-terminal regions that flank a core domain rich in alanine and glycine residues. After secretion and spinning by the spider, the spider silk matures into a semicrystalline material wherein regions of self-assembled regularly ordered domains are embedded in an amorphous matrix. The ordered domains consist of antiparallel beta-sheet crystals that are encoded by poly-(Gly-Ala) and poly-Ala repeats. Confined hydrogen bonding networks between these crystalline beta-sheets are thought to underpin the unique mechanical properties of silk (see, e.g., Keten, S., Xu, Z., Ihle, B. & Buehler, M. J., "Nanoconfinement controls stiffness, strength and mechanical toughness of β-sheet crystals in silk", *Nat. Mater.* 9, 359-367 (2010); and Nova, A., Keten, S., Pugno, N. M., Redaelli, A. & Buehler, M. J., "Molecular and nanostructural mechanisms of deformation, strength and toughness of spider silk fibrils", *Nano Lett.* 10, 2626-34 (2010)).

In some embodiments, the heterologous nucleic acid encoding the recombinant silk protein comprises a heterologous nucleic acid encoding a 1 to 150 repeats of a silk fibroin domain. In some embodiments, the recombinant silk protein comprises a 1 to 150 repeats of a silk fibroin domain. In some embodiments, the heterologous nucleic acid encoding the recombinant silk protein comprises a heterologous nucleic acid encoding a 2 to 64 repeats of a silk fibroin domain. In some embodiments, the recombinant silk protein comprises a 2 to 64 repeats of a silk fibroin domain. In some embodiments, the recombinant silk protein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 61, 63, 64, 65, 70, 75, 80, 85, 90, 95, 100, 105, 110, 115, 120, 125, 130, 135, 140, 145, or 150 silk fibroin domains. The combination of repeats of silk fibroin domain may comprise silk fibroin domains of the same type or of different types. In some embodiments, the silk fibroin domain is selected from the group consisting of a minor ampullate silk fibroin domain, an aggregate silk fibroin domain, a flagelliform (flag) silk fibroin domain, a tubulin silk fibroin domain, an aciniform silk fibroin domain and a piriform silk fibroin domain. In some embodiments, the silk fibroin domain comprises a consensus amino acid sequence as set forth in the sequence listing (see, e.g., Lewis (2006) *Chem. Rev.* 106(9): 3762-74, the entire contents of which are incorporated herein be reference). In some embodiments, the silk fibroin domain comprises the amino acid sequence GRGGLGGQGAGMAAAAAMGGAGQG-GYGGLGSQGTS (SEQ ID NO: 3).

In some embodiments, the silk fibroin domain comprises an amino acid sequence as set forth in NCBI Database Accession Numbers: AAT08436.1, ADM14316.1, ADM14324.1, ADM14315.1, ADM14325.1, OEH77770.1, GAP79055.1, AKJ27708.1, ABD66603.1, ABD66602.1, CAM32263.1, CAM32262.1, CAM32261.1, CAM32260.1, CAM32259.1, CAM32258.1, CAM32257.1, CAM32256.1, CAM32255.1, CAM32254.1, CAM32253.1, CAM32252.1, CAM32251.1, CAM32249.1, 2LTH_B, 2LTH_A, AGQ04592.1, CAM32272.1, ACC77633.1, 4FBS_A, 2LPJ_A, 2LPI_A, ABR68856.1, ABR68855.1, ACF19416.1, ACF19415.1, ACF19414.1, ACF19413.1, ACF19412.1, ACF19411.1, AAZ15372.1, AAZ15321.1, AEV46833.2, CAM32271.1, CAM32270.1, CAJ90517.1, AAZ15371.1, AAZ15320.1, AAZ15322.1, AAT75317.1, AAT75316.1, AAT75315.1, AAT75314.1, AAT75313.1, AAT75312.1, AAT75311.1, AAT75310.1, AAT75309.1, AAT75308.1, ADV40100.1, AD078764.1, ADM14319.1, ADM14314.1, ABY67415.1, ABY67411.1, ABY67405.1, ABY67403.1, ABY67401.1, AAY28936.1, AAY28935.1, AAK30615.1, AAK30614.1, AAK30609.1, AAK30608.1, AAK30607.1, AAK30606.1, AAK30604.1, AAK30601.1, AAK30596.1, AAK30592.1, ADE74592.1, AAK30602.1, AAK30595.1, CAJ00428.1, ABY67429.1, ABY67428.1, ABY67427.1, ABY67426.1, ABY67425.1, ABY67424.1, ABY67423.1, ABY67422.1, ABY67421.1, ABY67420.1, ABY67419.1, ABY67418.1, ABY67417.1, ABY67414.1, ABY67412.1, ABY67410.1, ABY67408.1, ABY67406.1, ABY67404.1, ABY67402.1, ABY67400.1, ABR68858.1, ABR68857.1, NP_001149975.2, ABD24295.1, ABD24294.1, AAT08435.1, AAT08434.1, AAT08433.1, AAT08432.1, CAM32269.1, CAM32268.1, CAM32267.1, CAM32266.1, CAM32265.1, CAM32264.1, AJM90221.1, XP_013227994.1, EGF91682.1, ABY67416.1, ABY67413.1, ABY67409.1, ABY67407.1, AAK30605.1, AAK30603.1, AAK30597.1, AAK30591.1, KYK63513.1, KYK63505.1, KYF45748.1, LAA03183.1, LAA04613.1, LAA08218.1, LAA09714.1, LAA10141.1, LAA12328.1, LAA15428.1, LAA16019.1, LAA15714.1, LAA16712.1, XP_013439532.1, XP_013337057.1, XP_013248467.1, CEL74577.1, CEL67190.1, CBZ53200.1, KFH04906.1, KFH04893.1, KFH00791.1, KFG64992.1, KFG53453.1, KFG53436.1, KFG50409.1, KFG31363.1, ESS28619.1, CDJ62170.1, CDJ53902.1, CDJ36084.1, CDJ60407.1, CDI75130.1, CDJ37156.1, CDI81984.1, AFW71573.1, AFP64859.1, EMD82476.1, XP_003883232.1, EGY00935.1, EGY00136.1, EGY00025.1, EGY00024.1, EGY00023.1, EGY00022.1, EGY00021.1, EGX99920.1, ACG37383.1, CAM32250.1, 2MX9_B, 2MX9_A, 2MX8_A, 2M0M_B, 2M0M_A, AFN54363.1, AFV31615.1, AAN85281.1, AAR13814.1, AAR13813.1, AAR13812.1, AAR13811.1, AAR13810.1, AAR13809.1, AAR13808.1, AAR13807.1, AAR13806.1, 2MFZ_B, 2MFZ_A, AGB35874.1, AFN54362.1, ADM14322.1, ADM14320.1, ACB29694.1, AFM29836.1, ADM14328.1, ADM14326.1, ADM14321.1, ADM14317.1, ABC72644.1, AAP88232.1, ABR37275.1, AAX30096.1, ADM14318.1, 5IZ2_Z, 5IZ2_A, 5IZ2_B, 2MAB_B, 2MAB_A, AHK09813.1, ACF71409.1, ACF71408.1, AAC04504.1, AAC14590.1, AAC14589.1, AMK48677.1, AMK48676.1, AMK48674.1, AAC04503.1, ACF71410.1, ACF71407.1, ADM35668.1, ADM14332.1, ADM14330.1, ABC72645.1, AAY28945.1, AAY28943.1, AAY28942.1, AAY28940.1, AAY28939.1, AAY28934.1, AAX45292.1, AAV48953.1, AAV48952.1, AAV48951.1, AAV48950.1, AAV48949.1, AAV48948.1, AAV48947.1, AAV48946.1, AAV48945.1, AAV48944.1, AAV48940.1, AAV48939.1, AAV48938.1, AAV48937.1, AAV48936.1, AAV48935.1, AAV48934.1, AAV48933.1, AAV48932.1, AAV48931.1, AAV48930.1, AAV48929.1, AAV48928.1, AAV48927.1, AAV48926.1, AAV48925.1, AAV48924.1, AAV48923.1, AAV48922.1, AAV48921.1, AAV48920.1, AAR83925.1, AAL32472.1, AAC38957.1, ABR37276.1, AFX83565.1, AFX83563.1, AFX83561.1, AFX83560.1, AFX83559.1, AFX83558.1, AHK09789.1, AHK09788.1, AHK09787.1, AHK09786.1, AHK09785.1, AHK09784.1, AHK09783.1, AHK09782.1, AHK09781.1, AHK09780.1, AHK09779.1, AHK09778.1, AHK09777.1, AHK09776.1, AHK09775.1, AHK09774.1, AHK09773.1, AHK09772.1, AHK09771.1, AHK09770.1, AHK09769.1, AHK09768.1, AHK09767.1, AHK09766.1, AHK09765.1, AHK09764.1, AHK09763.1, AFX83566.1, AFX83557.1, ABD24296.1, 3LR2_B, 3LR2_A, P19837.3, P46802.1, P46804.1, 3LRD_B, 3LRD_A, 3LR8_B, 3LR8_A, 3LR6_B, 3LR6_A, XP_015337966.1, XP_015926902.1, XP_015923885.1, XP_015915953.1, XP_015907747.1, XP_015907077.1, XP_015907076.1, XP_015907075.1, XP_015907074.1, XP_015907073.1, XP_015907072.1, XP_015907071.1, XP_015907070.1, XP_015907069.1, XP_015927451.1, AMF13980.1, AMF13979.1, XP_005329120.1, KFM79920.1, KFM79313.1, KFM74936.1, BAE86855.1, ADG57595.1, AAB60212.1, AAA17673.1, WP_018592840.1, AAC88554.1, AAC81918.1, AOH90403.1, ADM14313.1, ABW80568.1, ABW80567.1, ABW80566.1, ABW80565.1, ABW80563.1, ABD61600.1, ABD61599.1, ABD61597.1, ABD61596.1, ABD61594.1, ABD61593.1, ABD61592.1, ABD61591.1, ABD61590.1, ABD61589.1, ABD61588.1, AAL32375.1, ADG57596.1, ADG57593.1, AAA29380.2, ABR37274.1, AAK30613.1, AAK30611.1, AAK30600.1, AAK30599.1, 2N3E_A, XP_007493712.1, XP_007493711.1, XP_007493710.1, XP_015924996.1, XP_015910086.1, XP_015910083.1, XP_015910082.1, XP_015910081.1, XP_015910080.1, XP_015908848.1, KYK65898.1, CUJ63677.1, KYF39742.1, 10025810.1, XP_006470793.1, XP_015337967.1, ALM54786.1, WP_054444469.1, WP_046811332.1, KL017202.1, AJQ48468.1, KFM60634.1, EPT32613.1, EIW81425.1, CAJ20380.1, WP_043737320.1, AJN51722.1, AJN51680.1, AJN51679.1, AJL53619.1, AJL53618.1, AJL53617.1, AJL53507.1, KIL96307.1, KGH32759.1, AIU80193.1, AIU51173.1, BAP74122.1, KFH16126.1, KFH14329.1, KFH03307.1, KFG59505.1, KFG53981.1, KFG48063.1, KFG46978.1, KFG35613.1, KFG31970.1, WP_031207438.1, XP_007768770.1, AHH59767.1, ESS29295.1, ERL52248.1, CDF00959.1, CDE91356.1, EPR57584.1, AGP17343.1, WP_016418412.1, EPC00821.1, WP_008485474.1, AGH61341.1, AGH61340.1, AGH61339.1, AGH61338.1, AGH61337.1, AGH61336.1, AGH61335.1, AGH61334.1, AGH61333.1, AGH61332.1, AGH61331.1, AGH61330.1, AGH61329.1, AGH61328.1, AGH61327.1, AGF22332.1, AGF22331.1, AGF22330.1, AFX03498.1, 2KHM_B, 2KHM_A, EKE71000.1, AF002081.1, AF002080.1, ADG57597.1, AFM97627.1, AFM97625.1, AFM97623.1, AFM97621.1, AFM97619.1, AFM97618.1, AFM97617.1, AFM97616.1, AFM97615.1, AFL33148.1, ABW80562.1, AAC47011.1, AAC47010.1, AAC47009.1, AAC47008.1, AAA29381.1, AEQ78099.1, AEQ78098.1, AEQ44307.1, AEQ44306.1, AEQ44305.1, AEH19948.1, AEH19947.1, AEH19946.1, ADS13223.1, ADS13222.1, ADS13221.1, ACR88286.1, ACR88284.1, ACR88282.1, ACR88281.1, ACR88277.1, ACR88276.1, ACR88274.1, ACR88272.1, ACR88270.1, ACR88269.1, ACR88268.1, ACR88267.1, ACR88266.1, ACR88265.1, ACR88264.1, ACR88263.1, BAE86856.1, AAE50748.1, 1589022, 1589021, BAE51681.1, AOH90437.1, AOH90431.1, NP_628424.1, ACI23395.1, ADH65296.1, ADH65027.1, AAC38846.1, AAF36091.1, XP_015928803.1, XP_015926099.1, XP_015926098.1, XP_015925523.1, XP_015922043.1, XP_015918918.1, XP_015913485.1, XP_015912961.1, XP_015912814.1, XP_015664484.1, XP_015664483.1, AMF14002.1, AMF14001.1, AMF13994.1, AMF13992.1, AMF13991.1, AMF13990.1, CUW39853.1, KPA86045.1, KPA86044.1, BAS78900.1, XP_013416068.1, WP_052004167.1, ADR37091.1, ENH87197.1, KFM79464.1, KFM73910.1, KFM70693.1, KFM62633.1, KFM62627.1, KFM61802.1, KFM61798.1, KFM59473.1, KFM57717.1, EPE04573.1, CAB77344.1, ADU51385.1, ADU51096.1, ADU50755.1, ADU50701.1, ADU50272.1, WP_028670286.1, AHL56647.1, ADK84021.1, WP_010403048.1, WP_011385254.1, AFX83556.1, EME70738.1, 2K3Q_A, AAR21194.1, AAX83289.1, XP_002462408.1, BAE54451.1, CAJ90517.1, AAC38846.1, AAF36091.1, AEQ78099.1, AEQ78098.1, ADH65317.1, ADH65186.1, EFP05295.1, XP_003113957.1, AFV31615.1, AFM29836.1, ADM14322.1, ADM14320.1, ADM14328.1, ADM14326.1, ADM14321.1, AFV31614.1, AFV31613.1, AFM29835.1, ADM14329.1, ADM14327.1, LAA15038.1, 2M0M_B, 2M0M_A, 2MX9_B, 2MX9_A, 2MX8_A, 2MFZ_B, 2MFZ_A, ACB29694.1, AAC14590.1, AAC14589.1, ABC72645.1, ABR37276.1, 2MAB_B, 2MA_A, ADG57595.1, AAC88554.1, AAC81918.1, AMK48677.1, AMK48676.1, AMK48674.1, AMK48679.1, AMK48678.1, AMK48675.1, AMK48658.1, AMK48673.1, AMK48672.1, AMK48671.1, AMK48670.1, AMK48669.1, AMK48668.1, AMK48667.1, AMK48666.1, AMK48665.1, AMK48664.1, AMK48663.1, AMK48662.1, AMK48661.1, AMK48660.1, AMK48659.1, AFP57565.1, AFP57562.1, AFP57559.1, AAX45292.1, AAX45295.1, AAX45293.1, AAX45291.1, ANU43172.1, KOA64249.1, KOA59653.1, KOA54241.1, KOA52153.1, KOA48308.1, KOA44837.1, KOA44098.1, AJD89173.1, AJC77129.1, AGW85645.1, KFI80719.1, KFI77799.1, KFI56933.1, KFI41035.1, AIA33447.1, ACL28956.1, EHN17524.1, AAY28931.1, AAY28934.1, AAY28933.1, AAY28932.1, ADM14332.1, ADM14323.1, AAY28945.1, AAY28943.1, AAY28942.1, AAY28940.1, AAY28939.1, ADM14333.1, ADM14331.1, ADM14330.1, ABD24296.1, AAX45294.1, ADV40185.1, AAY28954.1, AAY28952.1, AAY28951.1, AAY28950.1, AAY28949.1, AAY28948.1, AAY28947.1, AAY28946.1, AAY28944.1, AAY28941.1, AAY28938.1, AAY28937.1, KFI66148.1, CDL70925.1, AFA43480.1, AAY28953.1, AFX83557.1, AAY28936.1, AAY28935.1, ABR68858.1, ABR68857.1, ABR37274.1, AFX83565.1, AFX83563.1, AFX83561.1, AFX83560.1, AFX83559.1, AFX83558.1, 2LYI_A, ABW24499.1, AFX83568.1, AFX83567.1, AFX83564.1, AFX83562.1, KFM79920.1, BAE86856.1, BAE86855.1, ABW80568.1, KFM62627.1, XP_015924996.1, XP_015907747.1, ABW80566.1, ABC72645.1, BAE54451.1, ABD61589.1, ABC72644.1, AAC14589.1, AAK30600.1, ACR88282.1, ACI23395.1, KFM70693.1, KFM62633.1, 2MAB_B, 2MAB_A, AAR83925.1, AHK09813.1, ADM35668.1, AFX83565.1, AFX83563.1, AFX83561.1, AFX83560.1, AFX83559.1, AFX83558.1, 2LYI_A, ABW24499.1, AHK09789.1, AHK09788.1, AHK09787.1, AHK09786.1, AHK09785.1, AHK09784.1, AHK09783.1, AHK09782.1, AHK09781.1, AHK09780.1, AHK09779.1, AHK09778.1, AHK09777.1, AHK09776.1, AHK09775.1, AHK09774.1, AHK09773.1, AHK09772.1, AHK09771.1, AHK09770.1, AHK09769.1, AHK09768.1, AHK09767.1, AHK09766.1, AHK09765.1, AHK09764.1, AHK09763.1, AFX83566.1, AFX83557.1, ADM35669.1, LAA01884.1, LAA09345.1, LAA09348.1, LAA15662.1, LAA16773.1, AHK09812.1, AHK09811.1, AHK09810.1, AHK09809.1, AHK09808.1, AHK09807.1, AHK09806.1, AHK09805.1, AHK09804.1, AHK09803.1, AHK09802.1, AHK09801.1, AHK09800.1, AHK09799.1, AHK09798.1, AHK09797.1, AHK09796.1, AHK09795.1, AHK09794.1, AHK09793.1, AFX83568.1, AFX83567.1, AFX83564.1, AFX83562.1, 2MU3_A, 307159084, 818905455, 347811351, 307159086, 307159082, and 301078347, the amino acid sequences corresponding to each accession number which are incorporated herein by reference.

In some embodiments, the silk fibroin domain comprises a minor ampullate silk fibroin domain. In some embodiments, the minor ampullate silk fibroin domain comprises an amino acid sequence as set forth in NCBI Database Accession Numbers: AAC14589.1, AAC14590.1, AAC14591.1, A0034847.1, A0034825.1, ACI63001.1, AIT41471.1, AGX00072.1, AGX00067.1, AGX00064.1, AGX00062.1, AGP47431.1, AGP47492.1, AG088936.1, AG088929.1, AG088926.1, AG088855.1, AG088848.1, AG088845.1, AAK62518.1, CUU33208.1, CUI09422.1, AJR18647.1, YP_008166902.1, YP_008161883.1, CTQ89448.1, CEL20537.1, YP_009062955.1, YP_009062950.1, YP_009062947.1, YP_009062945.1, YP_009023249.1, YP_009023242.1, YP_009023239.1, YP_009023168.1, YP_009023161.1, YP_009023158.1, NP_862422.1, YP_008145026.1, YP_002286943.1, CEF90318.1, CDF32058.1, 2MX9_B, 2MX9_A, 2MX8_A, 2M0M_B, 2M0M_A, 2MFZ_B, 2MFZ_A, ACB29694.1, AFV31615.1, ABC72645.1, ABR37276.1, ABR37278.1, ADM14328.1, ADM14326.1, ADM14321.1, ABR37277.1, ADM14322.1, ADM14320.1, ADM14329.1, ADM14327.1, 2MAB_B, 2MAB_A, ADG57595.1, AAC88554.1, AAC81918.1, 2MQA_A, AAC88595.1, AAC88594.1, AAC88593.1, AAC88592.1, AAC88591.1, AAC88590.1, AAC88589.1, AAC88588.1, AAC88587.1, AAC88586.1, AAC88585.1, AAC88584.1, AAC88583.1, AAC88582.1, AAC88581.1, AAC88580.1, AAC88579.1, AAC88578.1, AAC88577.1, AAC88576.1, AAC88575.1, AAC88574.1, AAC88573.1, AAC88572.1, AAC88571.1, AAC88570.1, AAC88569.1, AAC88568.1, AAC88567.1, AAC88566.1, AAC88565.1, AAC88564.1, AAC88563.1, AAC88562.1, AAC88561.1, AAC88560.1, AAC88559.1, AAC88558.1, AAC88557.1, AAC88556.1, AAC88555.1, AAC88553.1, AAC88552.1, AAC88551.1, AAC81959.1, AAC81958.1, AAC81957.1, AAC81956.1, AAC81955.1, AAC81954.1, AAC81953.1, AAC81952.1, AAC81951.1, AAC81950.1, AAC81949.1, AAC81948.1, AAC81947.1, AAC81946.1, AAC81945.1, AAC81944.1, AAC81943.1, AAC81942.1, AAC81941.1, AAC81940.1, AAC81939.1, AAC81938.1, AAC81937.1, AAC81936.1, AAC81935.1, AAC81934.1, AAC81933.1, AAC81932.1, AAC81931.1, AAC81930.1, AAC81929.1, AAC81928.1, AAC81927.1, AAC81926.1, AAC81925.1, AAC81924.1, AAC81923.1, AAC81922.1, AAC81921.1, AAC81920.1, AAC81919.1, AAC81917.1, AAC81916.1, and AAC81915.1, the amino acid sequences corresponding to each accession number which are incorporated herein by reference.

In some embodiments, the silk fibroin domain comprises an aggregate silk fibroin domain. In some embodiments, the aggregate silk fibroin domain comprises an amino acid sequence as set forth in NCBI Database Accession Numbers: AMK48658.1, AMK48673.1, AMK48672.1, AMK48671.1, AMK48670.1, AMK48669.1, AMK48668.1, AMK48667.1, AMK48666.1, AMK48665.1, AMK48664.1, AMK48663.1, AMK48662.1, AMK48661.1, AMK48660.1, AMK48659.1, AFP57565.1, AFP57562.1, AMK48679.1, AMK48678.1, AMK48677.1, AMK48676.1, AMK48675.1, and AMK48674.1, the amino acid sequences corresponding to each accession number which are incorporated herein by reference.

In some embodiments, the silk fibroin domain comprises a flagelliform (flag) silk fibroin domain. In some embodiments, the flagelliform (flag) silk fibroin domain comprises an amino acid sequence as set forth in NCBI Database Accession Numbers: AAC38846.1, AAT36347.1, AAC38847.1, AAF36091.1, AAK30594.1, AAK30593.1, AAF36092.1, AAF36090.1, AAF36089.1, EEC09351.1, EEC05390.1, ADN23579.1, ADN23577.1, KUG05367.1, AIY48668.1, CTQ93180.1, CRK58766.1, CRK58764.1, AJW39886.1, BAQ62602.1, KKW05526.1, EEC20124.1, EAX93621.1, CEL23644.1, KIG11542.1, EWC62749.1, EUA21042.1, EJI95902.1, XP_002433990.1, XP_002400080.1, XP_002401328.1, XP_001306551.1, BAC99451.1, ABR37273.1, ABK00016.1, CAJ90517.1, ADH65223.1, ADH65221.1, ADH65090.1, ADH65055.1, ADH65034.1, BAS78003.1, ADV61483.1, AEB08848.1, ADU52289.1, ADU51393.1, BAF18870.1, BAF08409.1, BAG95178.1, and CAB87946.1, the amino acid sequences corresponding to each accession number which are incorporated herein by reference.

In some embodiments, the silk fibroin domain is a tubulin silk fibroin domain. In some embodiments, the tubulin silk fibroin domain comprises an amino acid sequence as set forth in NCBI Database Accession Numbers: JAR06716.1, BAE86856.1, BAE86855.1, AAY28931.1, 2K3O_A, 2K3N_A, AAY28933.1, AAY28932.1, BAE54450.1, AAY28934.1, AAX45295.1, AAX45293.1, AAX45291.1, BAE54451.1, ABR37274.1, ACI23395.1, ADM14323.1, ABD24296.1, ADM14332.1, AAX45292.1, AAC14589.1, ADV40185.1, ADM14333.1, ADM14331.1, AAY28954.1, AAY28952.1, AAY28951.1, AAY28950.1, AAY28949.1, AAY28948.1, AAY28947.1, AAY28946.1, AAY28945.1, AAY28944.1, AAY28943.1, AAY28942.1, AAY28941.1, AAY28940.1, AAY28939.1, AAY28938.1, AAY28937.1, ADM14330.1, AAX45294.1, AFA43480.1, AAY28953.1, KFM79920.1, AFX83557.1, AGR65217.1, WP_020843129.1, AFM97620.1, ABW80568.1, KFM62627.1, AAZ15706.1, AAK30612.1, ACR88285.1, ABD61598.1, AAY90151.1, ABR68858.1, ABR68857.1, ABW80564.1, AAY28936.1, AAY28935.1, ABD61589.1, XP_015924996.1, KXT76149.1, ABW80566.1, ABC72645.1, ABN13925.1, XP_015907747.1, ABR37278.1, CUR40212.1, KTF81708.1, XP_014025605.1, XP_014025604.1, XP_014025602.1, ABW24499.1, ADV40181.1, ABC72644.1, AAK30600.1, KFM70693.1, KFM62633.1, AHK09791.1, AFX83568.1, AFX83567.1, AFX83565.1, AFX83564.1, AFX83563.1, AFX83562.1, AFX83561.1, AFX83560.1, AFX83559.1, AFX83558.1, ACR88282.1, EOY18426.1, ADU23756.1, EAQ83169.1, ACV03419.1, EDW00619.1, KZN71099.1, WP_062906493.1, WP_062896115.1, ALU60113.1, XP_006990705.2, KXZ53453.1, KXT17944.1, KXT08739.1, XP_015495616.1, XP_015472967.1, XP_015472966.1, XP_015472964.1, XP_015472963.1, XP_015472962.1, XP_015472961.1, CUR39570.1, XP_015338007.1, XP_015338006.1, GAC97239.1, XP_002000489.1, CUU27780.1, XP_014781761.1, XP_014773071.1, XP_014794002.1, XP_014794001.1, XP_014794000.1, XP_014726746.1, XP_014726745.1, XP_014726744.1, WP_011723794.1, CUI03994.1, WP_057406778.1, EDW15950.1, KPX62564.1, XP_008545413.1, KPI97631.1, WP_054263331.1, XP_014167486.1, XP_014116011.1, XP_014122317.1, XP_014122316.1, XP_014112343.1, XP_014030156.1, XP_014030155.1, XP_014030153.1, XP_014025603.1, XP_014054492.1, XP_013676349.1, KOF87513.1, KOF87511.1, WP_050780405.1, WP_042229582.1, WP_051870755.1, WP_051863026.1, WP_051861131.1, KEQ92117.1, XP_013340518.1, XP_013227263.1, XP_013227262.1, XP_013227261.1, XP_013153866.1, XP_005463415.1, CRH97187.1, XP_013034801.1, XP_012994535.1, XP_012994534.1, XP_012994533.1, XP_012994532.1, XP_012950187.1, XP_012950183.1, 2MQA_A, XP_012670522.1, AKI80407.1, WP_046357626.1, KKE81922.1, XP_012190826.1, KFM77639.1, EKX40791.1, EGX96200.1, XP_011413944.1, CEK40236.1, XP_011315453.1, JAG80700.1, KIM38534.1, CAQ41616.1, WP_036204683.1, KHN36369.1, CCQ38052.1, XP_010005229.1, CDY50596.1, CDG98384.1, CDH00697.1, CDH18149.1, WP_030453286.1, KEQ48985.1, CDP19197.1, WP_026128052.1, WP_024859189.1, AGR65376.1, XP_007910174.1, XP_007905153.1, YP_008873468.1, EYB28497.1, AGI11726.1, XP_006818343.1, XP_006807688.1, XP_006807687.1, XP_006807686.1, ABK65722.1, XP_006666077.1, XP_005827771.1, WP_021434916.1, EQK53805.1, WP_018500291.1, WP_010166019.1, WP_015410778.1, WP_013483306.1, 2LYI_A, YP_001426738.1, XP_001985752.1, EFA85813.1, XP_002260349.1, XP_001613854.1, XP_001226254.1, ABT16391.1, and EDL44127.1, the amino acid sequences corresponding to each accession number which are incorporated herein by reference.

In some embodiments, the silk fibroin domain is an aciniform silk fibroin domain. In some embodiments, the aciniform silk fibroin domain comprises an amino acid sequence as set forth in NCBI Database Accession Numbers: AFX83557.1, 2MU3_A, 2MAB_B, 2MAB_A, ABW24499.1, AAR83925.1, AHK09813.1, AHK09791.1, AHK09789.1, AHK09788.1, AHK09787.1, AHK09786.1, AHK09785.1, AHK09784.1, AHK09783.1, AHK09782.1, AHK09781.1, AHK09780.1, AHK09779.1, AHK09778.1, AHK09777.1, AHK09776.1, AHK09775.1, AHK09774.1, AHK09773.1, AHK09772.1, AHK09771.1, AHK09770.1, AHK09769.1, AHK09768.1, AHK09767.1, AHK09766.1, AHK09765.1, AHK09764.1, AHK09763.1, AFX83568.1, AFX83567.1, AFX83566.1, AFX83565.1, AFX83564.1, AFX83563.1, AFX83562.1, AFX83561.1, AFX83560.1, AFX83559.1, AFX83558.1, 2LYI_A, AHK09812.1, AHK09811.1, AHK09810.1, AHK09809.1, AHK09808.1, AHK09807.1, AHK09806.1, AHK09805.1, AHK09804.1, AHK09803.1, AHK09802.1, AHK09801.1, AHK09800.1, AHK09799.1, AHK09798.1, AHK09797.1, AHK09796.1, AHK09795.1, AHK09794.1, AHK09793.1, AHK09792.1, and AHK09790.1, the amino acid sequences corresponding to each accession number which are incorporated herein by reference.

In some embodiments, the silk fibroin domain is a piriform silk fibroin domain. In some embodiments, the piriform silk fibroin domain comprises an amino acid sequence as set forth in NCBI Database Accession Numbers: AEP25627.1, ADN39427.1, ADN39425.1, ADN39426.1, and ADK56477.1, the amino acid sequences corresponding to each accession number which are incorporated herein by reference.

Methods of the present invention use the curli fiber production systems of a bacterium, such as *E. coli* to produce curli fibers formed using recombinant silk proteins described herein that comprise an amyloid domain (e.g., CsgA) Curli fibers are the primary proteinaceous structural component of *E. coli* biofilms. They are highly robust functional amyloid nanofibers with a diameter of approximately 4-7 nm that exist as extended tangled networks encapsulating the cells. Curli fibers or curli are formed from the extracellular self-assembly of CsgA, a small secreted 13-kDa protein (see, e.g., Chapman, M. R. et al. Role of *Escherichia coli* curli operons in directing amyloid fiber formation. *Science* 295, 851-855 (2002)). A homologous outer-membrane protein, CsgB, nucleates CsgA assembly and also anchors the nanofibers to the bacterial surface. Detached curli fibers can also exist as non-cell associated structural components of the extracellular matrix (ECM). The curli genes exist as two divergently transcribed operons (csgBAC and csgDEFG), whose seven products mediate the structure (CsgA), nucleation (CsgB), processing (CsgE, F), secretion (CsgC, G), and direct transcriptional regulation (CsgD) of curli nanofibers. This curli secretion system is considered a distinct secretion system of its own in gram-negative bacterium and is named the Type-VIII secretion system (T8SS) (see, e.g., Desvaux et al., *Trends Microbiol.* 17, 139-45 (2009), which is hereby incorporated by reference in its entirety). Thus, in some embodiments, the heterologous nucleic acid encoding a recombinant silk protein further comprises a heterologous nucleic acid encoding an amyloid domain. In some embodiments, the recombinant silk protein further comprises an amyloid domain. In some embodiments, the amyloid domain comprises CsgA.

Aspects of the present disclosure are directed to the use of a secretion system, such as a T8SS secretion system, to export a recombinant silk polypeptide disclosed herein, such as a recombinant silk protein comprising a spider silk fibroin domain, from within a bacterium (such as a gram-negative or gram-positive bacterium) and into the surrounding environment. According to one aspect, the recombinant silk protein is an amyloid-silk hybrid, for example, comprises a silk fibroin domain connected (i.e., fused) to an amyloid domain (e.g., CsgA). According to this aspect, the recombinant silk protein is secreted into the extracellular space or milieu of the bacterium. The secreted recombinant silk protein can then be collected and purified. According to one aspect, the recombinant silk protein can comprise one or more of an amyloid, elastin, or collagen domains to alter the physical and mechanical properties of the resulting material as compared to a recombinant silk protein that does not comprise an amyloid, elastin, or collagen domain.

In one aspect, provided herein is an engineered bacterium comprising a heterologous nucleic acid sequence encoding a recombinant silk protein, wherein the recombinant silk protein comprises a periplasmic translocation signal sequence, an outer membrane secretion signal sequence, a silk fibroin domain and one or more of an amyloid domain, an elastin domain or a collagen domain. In some embodiments, the amyloid domain is CsgA.

In another aspect, provided herein is a nucleic acid sequence encoding a recombinant silk protein described herein. In one embodiment, provided herein is a nucleic acid sequence encoding a recombinant silk protein, wherein the recombinant silk protein comprises a periplasmic translocation signal sequence, an outer membrane secretion signal sequence, a silk fibroin domain and one or more of an amyloid domain, an elastin domain or a collagen domain. In some embodiments, the amyloid domain is CsgA.

In yet another aspect, provided herein is a recombinant silk protein comprising a periplasmic translocation signal sequence, an outer membrane secretion signal sequence, a silk fibroin domain and one or more of an amyloid domain, an elastin domain or a collagen domain. In some embodiments, the periplasmic translocation signal sequence and/or the outer membrane secretion signal sequence is cleaved-off the recombinant silk protein within the cell. In some embodiments, the amyloid domain is CsgA.

As used herein, "CsgA" refers to the major structural subunit of curli. The sequences of CsgA and its homologs are known in a number of species, e.g., the sequence of *E. coli* CsgA is known (NCBI Gene ID NO: 949055; (SEQ ID NO: 4) (polypeptide)).

```
CsgA polypeptide (NCBI Ref Seq: NP 415560)
                                                    (SEQ ID NO: 4)
    1  mkllkvaaia aivfsgsala gvvpqygggg nhggggnnsg pnselniyqy gggnsalalq 61  tdarnsdlti tqhgggngad vgqgsddssi dltqrgfgns atldqwngkn semtvkqfgg 121  gngaavdqta snssvnvtqv gfgnnatahq y.
```

In some embodiments, "CsgA" refers to an *E. coli* CsgA. In some embodiments, "CsgA" refers to a polypeptide having at least 80% homology to SEQ ID NO: 4 (e.g., 80% or greater homology, 90% or greater homology, or 95% or greater homology), e.g. naturally occurring mutations or variants of CsgA, homologs of CsgA, or engineered mutations or variants of CsgA. In some embodiments, CsgA refers to a polypeptide comprising an amino acid sequence having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of SEQ ID NO: 4. The silk fibroin domain may be directly connected to the CsgA polypeptide or be connected via a linker at either the C-terminus or the N-terminus or both of the CsgA, but without interrupting the sequence of the CsgA polypeptide. CsgA within the scope of the present disclosure includes an amyloid domain which self-assembles into an amyloid structure. According to certain aspects, a linker may be attached to either the C-terminus or the N-terminus or separate linkers may be attached to both the C terminus and the N terminus of the CsgA.

According to one aspect, self-assembling protein domains, such as CsgA, are used to generate the similar self-assembling characteristics for artificial silk fusion proteins. A factor in the maturation of spider silk in spiders is the self-assembly of N- and C-terminal domains intiated by changes in pH and ionic strength (see, e.g., Gronau et al. (2013) *Biomater. Sci.* 1(3): 276-84; Hagn et al. (2010) *Nature* 465(7295): 239-42; Schwarze et al. (2013) *Nat. Commun.* 4: 2815). These changes in the spider's silk glands lead to the step-wise assembly of the silk proteins from a stored nematic liquid to a super strong biofilament. Replicating this assembly of the silk proteins into a strong fiber has been a key step towards replicating the amazing physical properties of spider silk. According to the present disclosure, the pH/salt driven assembly of the N- and C-terminal domains is replaced with other self-assembling protein domains, such as CsgA, to generate the similar self-assembling characteristics for artificial silk fusion proteins.

According to one aspect, engineered bacteria are modified to comprise a heterologous nucleic acid encoding the recombinant silk protein described herein (e.g., a recombinant silk protein comprising an amyloid domain such as CsgA). In some embodiments, the recombinant silk protein comprises an elastin domain or a collagen domain. Useful sequences and structures for elastin domains and collagen domains are known to those of skill in the art, such as VPVXG (SEQ ID NO: 5) which is an exemplary elastin domain.

The polypeptide, such as spider silk, may also be connected to a domain which guides the polypeptide to the periplasm and/or a domain which guides the polypeptide outside of the bacterium through the outer cell wall. Methods of introducing a nucleic acid to a bacteria cell are known to those of skill in the art. In some embodiments, the engineered bacterium is modified to comprise a heterologous nucleic acid encoding a recombinant silk protein described herein, wherein the heterologous nucleic acid is located in the bacterial chromosome. In some embodiments, the engineered bacterium is modified to comprise a heterologous nucleic acid encoding a recombinant silk protein described herein, wherein the heterologous nucleic acid is located in a plasmid.

According to one aspect, the engineered bacteria secrete the recombinant silk protein, such that the protein is free for collection and purification. According to one aspect, the modified bacteria secrete the recombinant silk protein resulting in curli fiber production. In another aspect, biofilms comprising the recombinant silk protein described herein, or an engineered bacteria described herein are provided.

In some embodiments, the recombinant silk protein (e.g., recombinant spider silk or recombinant CsgA-spider silk fusion) may be produced by engineered or non-naturally occurring bacteria. According to one aspect, methods are provided for engineering a bacteria to produce a recombinant silk protein (e.g., a recombinant silk protein not comprising an amyloid domain or a recombinant silk protein comprising an amyloid domain) which may be exported from the bacterium. The recombinant silk protein comprising an amyloid domain (e.g., CsgA, which is also referred to herein as a CsgA-spider silk fusion protein) may be exported from the bacterium and assemble into extracellular amyloid fibers. After secretion, the CsgA-spider silk fusion protein may nucleated to form an amyloid at the cell surface, polymerize into long fibers, and optionally, eventually encapsulate the bacterium, and provide a biofilm with structural support. In some embodiments, provided herein are biofilms comprising an engineered bacterium as described herein.

CsgA within the scope of the present disclosure includes an amyloid domain which self-assembles into an amyloid structure. According to certain aspects, a linker may be attached to either the C terminus or the N-terminus or separate linkers may be attached to both the C terminus and the N terminus.

Aspects of the present disclosure are directed to a method of producing a genetically modified bacterium including genetically altering a bacterium having one or more genomic nucleic acids encoding a polypeptide secretion system to include an exogenous nucleic acid encoding a recombinant protein including a domain for periplasmic localization, a domain for directing the recombinant protein to the outer membrane for secretion and one or more silk fibroin domains, wherein the exogenous nucleic acid is under operation of a promoter to express the recombinant protein. According to one aspect, the polypeptide secretion system is a Type VIII secretion system or a HlyA Type 1 secretion system. According to one aspect, the polypeptide secretion system includes a periplasmic secretion system and a system for secretion through the outer membrane of the bacterium. According to one aspect, the polypeptide secretion system includes a periplasmic secretion system and a system for secretion through the outer membrane of the bacterium and wherein the periplasmic secretion system is a Sec system. According to one aspect, the polypeptide secretion system includes a periplasmic secretion system and a system for secretion through the outer membrane of the bacterium and wherein the periplasmic secretion system is a twin-arginine translocation (Tat) system. According to one aspect, the polypeptide secretion system includes a periplasmic secretion system and a system for secretion through the outer membrane of the bacterium and wherein the periplasmic secretion system is a signal recognition particle (SRP) system. According to one aspect, the polypeptide secretion system includes a periplasmic secretion system and a system for secretion through the outer membrane of the bacterium and a domain for periplasmic localization is a Sec domain or a Tat domain or a signal recognition particle domain. According to one aspect, the polypeptide secretion system includes a periplasmic secretion system and a system for secretion through the outer membrane of the bacterium and a domain for periplasmic localization is a component of a Sec system, a component of a Tat system or a component of a signal recognition particle system. According to one aspect, the polypeptide secretion system includes a periplasmic secretion system and a system for secretion through the outer membrane of the bacterium and wherein the system for secretion through the outer membrane of the bacterium is a N22 system. According to one aspect, the polypeptide secretion system includes a periplasmic secretion system and a system for secretion through the outer membrane of the bacterium and wherein the system for secretion through the outer membrane of the bacterium is a YebF system. According to one aspect, the polypeptide secretion system includes a periplasmic secretion system and a system for secretion through the outer membrane of the bacterium and wherein a domain for directing the recombinant protein to the outer membrane for secretion is an N22 domain or a YebF domain. According to one aspect, the exogenous nucleic acid further encodes the recombinant protein to include one or more of an amyloid domain, an elastin domain or a collagen domain. According to one aspect, the exogenous nucleic acid further encodes the recombinant protein to include a CsgA domain. According to one aspect, the bacterium is E. coli. According to one aspect, the bacterium is non-pathogenic. According to one aspect, the silk fibrin domain includes the amino acid sequence GRGGLGGQGAGMAAAAAMGGAGQGGYGGLGSQGTS (SEQ ID NO:3). According to one aspect, the silk fibrin domain includes 4 to 64 repeats of the amino acid sequence (SEQ ID NO: 3)
GRGGLGGQGAGMAAAAAMGGAGQGGYGGLGSQGTS.

Aspects of the present disclosure are directed to a method for producing one or more silk fibroin domains from a genetically modified bacterium including providing the genetically modified bacterium in culture media conditions, wherein the genetically modified bacterium includes one or more genomic nucleic acids encoding a polypeptide secretion system and further including an exogenous nucleic acid encoding a recombinant protein including a domain for periplasmic localization, a domain for directing the recombinant protein to the outer membrane for secretion and the one or more silk fibroin domains, wherein the exogenous nucleic acid is under operation of a promoter to express the recombinant protein, and expressing the exogenous nucleic acid to produce the recombinant protein wherein the recombinant protein is secreted from the bacterium and into the surrounding culture media. According to one aspect, the method further provides proliferating the bacterium to produce a population of bacteria cells expressing the exogenous nucleic acid. According to one aspect, the method further provides proliferating the bacterium to produce a population of bacteria cells expressing the exogenous nucleic acid to form a biofilm including the recombinant protein. According to one aspect, the polypeptide secretion system is a Type VIII secretion system or a HlyA Type 1 secretion system. According to one aspect, the polypeptide secretion system includes a periplasmic secretion system and a system for secretion through the outer membrane of the bacterium. According to one aspect, the polypeptide secretion system includes a periplasmic secretion system and a system for secretion through the outer membrane of the bacterium and wherein the periplasmic secretion system is a Sec system. According to one aspect, the polypeptide secretion system includes a periplasmic secretion system and a system for secretion through the outer membrane of the bacterium and wherein the periplasmic secretion system is a twin-arginine translocation (Tat) system. According to one aspect, the polypeptide secretion system includes a periplasmic secretion system and a system for secretion through the outer membrane of the bacterium and wherein the periplasmic secretion system is a signal recognition particle (SRP) system. According to one aspect, the polypeptide secretion system includes a periplasmic secretion system and a system for secretion through the outer membrane of the bacterium and a domain for periplasmic localization is a Sec domain or a Tat domain or a signal recognition particle domain. According to one aspect, the polypeptide secretion system includes a periplasmic secretion system and a system for secretion through the outer membrane of the bacterium and a domain for periplasmic localization is a component of a Sec system, a component of a Tat system or a component of a signal recognition particle system. According to one aspect, the polypeptide secretion system includes a periplasmic secretion system and a system for secretion through the outer membrane of the bacterium and wherein the system for secretion through the outer membrane of the bacterium is a N22 system. According to one aspect, the polypeptide secretion system includes a periplasmic secretion system and a system for secretion through the outer membrane of the bacterium and wherein the system for secretion through the outer membrane of the bacterium is a YebF system. According to one aspect, the polypeptide secretion system includes a periplasmic secretion system and a system for secretion through the outer membrane of the bacterium and wherein a domain for directing the recombinant protein to the outer membrane for secretion is an N22 domain or a YebF domain. According to one aspect, the exogenous nucleic acid further encodes the recombinant protein to include one or more of an amyloid domain, an elastin domain or a collagen domain. According to one aspect, the exogenous nucleic acid further encodes the recombinant protein to include a CsgA domain. According to one aspect, the bacterium is *E. coli*. According to one aspect, the bacterium is non-pathogenic. According to one aspect, the silk fibrin domain includes the amino acid sequence GRGGLGGQGAGMAAAAAMGGAGQGGYGGLGSQGTS (SEQ ID NO:3). According to one aspect, the silk fibrin domain includes 4 to 64 repeats of the amino acid sequence GRGGLGGQGAGMAAAAAMGGAGQGGYGGLGSQGTS (SEQ ID NO:3). According to one aspect, the exogenous nucleic acid further encodes the recombinant protein to include one or more functional proteins. According to one aspect, the exogenous nucleic acid further encodes the recombinant protein to include one or more functional proteins comprising an enzyme, an antibody or a detectable protein. According to one aspect, the recombinant protein is unattached to the bacterium. According to one aspect, the recombinant protein is attached to the bacterium.

Aspects of the present disclosure are directed to a genetically modified bacterium including one or more genomic nucleic acids encoding a polypeptide secretion system and further including an exogenous nucleic acid encoding a recombinant protein including a domain for periplasmic localization, a domain for directing the recombinant protein to the outer membrane for secretion and one or more silk fibroin domains, wherein the exogenous nucleic acid is under operation of a promoter to express the recombinant protein. According to one aspect, the polypeptide secretion system is a Type VIII secretion system or a HlyA Type 1 secretion system. According to one aspect, the polypeptide secretion system includes a periplasmic secretion system and a system for secretion through the outer membrane of the bacterium. According to one aspect, the polypeptide secretion system includes a periplasmic secretion system and a system for secretion through the outer membrane of the bacterium and wherein the periplasmic secretion system is a Sec system. According to one aspect, the polypeptide secretion system includes a periplasmic secretion system and a system for secretion through the outer membrane of the bacterium and wherein the periplasmic secretion system is a twin-arginine translocation (Tat) system. According to one aspect, the polypeptide secretion system includes a periplasmic secretion system and a system for secretion through the outer membrane of the bacterium and wherein the periplasmic secretion system is a signal recognition particle (SRP) system. According to one aspect, the polypeptide secretion system includes a periplasmic secretion system and a system for secretion through the outer membrane of the bacterium and a domain for periplasmic localization is a Sec domain or a Tat domain or a signal recognition particle domain. According to one aspect, the polypeptide secretion system includes a periplasmic secretion system and a system for secretion through the outer membrane of the bacterium and a domain for periplasmic localization is a component of a Sec system, a component of a Tat system or a component of a signal recognition particle system. According to one aspect, the polypeptide secretion system includes a periplasmic secretion system and a system for secretion through the outer membrane of the bacterium and wherein the system for secretion through the outer membrane of the bacterium is a N22 system. According to one aspect, the polypeptide secretion system includes a periplasmic secretion system and a system for secretion through the outer membrane of the bacterium and wherein the system for secretion through the outer membrane of the bacterium is a YebF system. According to one aspect, the polypeptide secretion system includes a periplasmic secretion system and a system for secretion through the outer membrane of the bacterium and wherein a domain for directing the recombinant protein to the outer membrane for secretion is an N22 domain or a YebF domain. According to one aspect, the exogenous nucleic acid further encodes the recombinant protein to include one or more of an amyloid domain, an elastin domain or a collagen domain. According to one aspect, the exogenous nucleic acid further encodes the recombinant protein to include a CsgA domain. According to one aspect, the bacterium is E. coli. According to one aspect, the bacterium is non-pathogenic. According to one aspect, the silk fibrin domain includes the amino acid sequence GRGGLGGQGAGMAAAAAMGGAGQGGYG-GLGSQGTS (SEQ ID NO:3). According to one aspect, the silk fibrin domain includes 4 to 64 repeats of the amino acid sequence GRGGLGGQGAGMAAAAAMGGAGQGGYG-GLGSQGTS (SEQ ID NO:3). According to one aspect, the exogenous nucleic acid further encodes the recombinant protein to include one or more functional proteins. According to one aspect, the exogenous nucleic acid further encodes the recombinant protein to include one or more functional proteins comprising an enzyme, an antibody or a detectable protein. According to one aspect, the recombinant protein is unattached to the bacterium. According to one aspect, the recombinant protein is attached to the bacterium.

In some embodiments, the heterologous nucleic acid encoding a recombinant silk protein further comprises a heterologous nucleic acid encoding a functional protein. In some embodiments, the heterologous nucleic acid encoding a recombinant silk protein further comprises one or more (e.g., two, three, four, five, six, or more) heterologous nucleic acid encoding a functional protein. In some embodiments, the recombinant silk protein further comprises a functional protein domain (e.g., the recombinant silk protein is fused to a functional protein described herein). In some embodiments, the recombinant silk protein comprises one or more (e.g., two, three, four, five, six, or more) functional proteins. In some embodiments, the functional protein comprises an enzyme, an antibody, a detectable protein, or a fragment thereof. In some embodiments, the detectable protein is a poly-histidine tag, a myc tag a FLAG tag, a hemagglutinin (HA) tag, or a V5 tag.

In some embodiments, the heterologous nucleic acid encoding a recombinant silk protein further comprises a heterologous nucleic acid encoding a protease cleavage site amino acid sequence. In some embodiments, the recombinant silk protein further comprises a protease cleavage site amino acid sequence. The protease cleavage site amino acid sequence may be disposed at any location between the multiple domains of the recombinant silk protein, including for example: between a periplasmic translocation signal sequence and an outer membrane secretion signal sequence, between an outer membrane secretion signal sequence and a silk fibroin domain, between a periplasmic translocation signal sequence and a silk fibroin domain, between an outer membrane secretion signal sequence and an amyloid domain, between a periplasmic translocation signal sequence and an amyloid domain, between a first silk fibroin domain and a second silk fibroin domain, between a silk fibroin domain and an amyloid domain, between an amyloid domain and a functional protein, between a silk fibroin domain and a functional protein.

In some embodiments, the heterologous nucleic acid encoding a recombinant silk protein further comprises a heterologous nucleic acid encoding a linker sequence. In some embodiments, the recombinant silk protein further comprises a linker sequence. The linker sequence may be disposed at any location between the multiple domains of the recombinant silk protein, including for example: between a periplasmic translocation signal sequence and an outer membrane secretion signal sequence, between an outer membrane secretion signal sequence and a silk fibroin domain, between a periplasmic translocation signal sequence and a silk fibroin domain, between a first silk fibroin domain and a second silk fibroin domain, between a silk fibroin domain and an amyloid domain, between an amyloid domain and a functional protein, between a silk fibroin domain and a functional protein.

Aspects of the present disclosure are directed to a non-naturally occurring protein including a fusion of a domain for periplasmic localization of the protein to periplasm of a bacterium, a domain for directing the protein to the outer membrane of a bacterium for secretion and one or more silk fibroin domains.

Aspects of the present disclosure are directed to a nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains.

Aspects of the present disclosure are directed to a vector comprising a nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains.

In one aspect, described herein are vectors comprising a heterologous nucleic acid described herein (e.g., a heterologous nucleic acid encoding a recombinant silk protein, wherein the recombinant silk protein comprises a periplasmic translocation signal sequence, an outer membrane secretion signal sequence, a silk fibroin domain, and optionally, one or more of an amyloid domain, an elastin domain, and a collagen domain).

Aspects of the present disclosure are directed to a bacterium including a foreign or exogenous nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains.

Aspects of the present disclosure are directed to a bacterium including a vector comprising a foreign or exogenous nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains.

Aspects of the present disclosure are directed to a bacterium expressing a foreign or exogenous nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains.

Aspects of the present disclosure are directed to a biofilm including a bacterium expressing a foreign or exogenous nucleic acid sequence encoding a non-naturally occurring protein including a fusion of a domain for periplasmic localization of the protein to periplasm of a bacterium, a domain for directing the protein to the outer membrane of a bacterium for secretion and one or more silk fibroin domains.

A "vector" includes a nucleic acid construct designed for delivery to a host cell or transfer between different host cells (e.g., a bacterial cell described herein). A vector can be viral or non-viral. Many vectors useful for transferring genes into target cells are available, e.g., the vectors may be episomal, e.g., plasmids, virus-derived vectors, or may be integrated into the target cell genome, through homologous recombination or random integration.

In some embodiments, a vector can be an expression vector. An "expression vector" can be a vector that has the ability to incorporate and express heterologous nucleic acid fragments in a cell. An expression vector may comprise additional elements, for example, the expression vector may have two replication systems, thus allowing it to be maintained in two organisms. The nucleic acid incorporated into the vector can be operably-linked to an expression control sequence when the expression control sequence controls and regulates the transcription and translation of that polynucleotide sequence.

In some embodiments, a heterologous nucleic acid encoding a recombinant silk protein, wherein the recombinant silk protein comprises a periplasmic translocation signal sequence, an outer membrane secretion signal sequence, and a silk fibroin domain; or a nucleic acid encoding a recombinant protein including one or more silk fibroin domains and one or more of a domain for periplasmic localization, a domain for directing the recombinant protein to the outer membrane for secretion, or a functional polypeptide such as an amyloid domain, an elastin domain or a collagen domain; can be present within a portion of a plasmid. Plasmid vectors include, but are not limited to, pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see Studier et al., "Use of T7 RNA Polymerase to Direct Expression of Cloned Genes," Gene Expression Technology, vol. 185 (1990), which is hereby incorporated by reference in its entirety).

A "viral vector" may be a nucleic acid vector construct that includes at least one element of viral origin and has the capacity to be packaged into a viral vector particle. The viral vector can contain a transgenic gene in place of non-essential viral genes. The vector and/or particle may be utilized for the purpose of transferring any nucleic acids into cells either in vitro or in vivo. Numerous viral vectors are known in the art and can be used as carriers of a nucleic acid into a cell, e.g. lambda vector system gt11, gt WES.tB, Charon 4.

In some embodiments, a heterologous nucleic acid described herein; such as a nucleic acid encoding a recombinant protein including one or more silk fibroin domains and one or more of a domain for periplasmic localization, a domain for directing the recombinant protein to the outer membrane for secretion, or a functional polypeptide such as an amyloid domain, an elastin domain or a collagen domain; can be constitutively expressed. In some embodiments, a heterologous nucleic acid described herein can be operably-linked to a constitutive promoter. In some embodiments, the heterologous nucleic acid described herein can be inducibly-expressed. In some embodiments, the heterologous nucleic acid described herein can be operably linked to an inducible promoter. In some embodiments, the heterologous nucleic acid described herein can be operably-linked to a native CsgA promoter.

An "inducible promoter" may be one that is characterized by initiating or enhancing transcriptional activity when in the presence of, influenced by, or contacted by an inducer or inducing agent than when not in the presence of, under the influence of, or in contact with the inducer or inducing agent. An "inducer" or "inducing agent" may be endogenous, or a normally exogenous compound or protein that is administered in such a way as to be active in inducing transcriptional activity from the inducible promoter. In some embodiments, the inducer or inducing agent, e.g., a chemical, a compound or a protein, can itself be the result of transcription or expression of a nucleic acid sequence (e.g., an inducer can be a transcriptional repressor protein), which itself may be under the control or an inducible promoter. Non-limiting examples of inducible promoters include but are not limited to, the lac operon promoter, a nitrogen-sensitive promoter, an IPTG-inducible promoter, a salt-inducible promoter, and tetracycline, steroid-responsive promoters, rapamycin responsive promoters and the like. Inducible promoters for use in prokaryotic systems are well known in the art, see, e.g., the beta-lactamase and lactose promoter systems (Chang et al., *Nature,* 275: 615 (1978), which is incorporated herein by reference); Goeddel et al., *Nature,* 281: 544 (1979), which is incorporated herein by reference), the arabinose promoter system, including the araBAD promoter (Guzman et al., *J. Bacteriol.,* 174: 7716-7728 (1 992), which is incorporated herein by reference; Guzman et al., *J. Bacteriol.,* 177: 4121-4130 (1995), which is incorporated herein by reference; Siegele and Hu, *Proc. Natl. Acad. Sci. USA,* 94: 8168-8172 (1997), which is incorporated herein by reference), the rhamnose promoter (Haldimann et al., *J. Bacteriol.,* 180: 1277-1286 (1998), which is incorporated herein by reference), the alkaline phosphatase promoter, a tryptophan (trp) promoter system (Goeddel, *Nucleic Acids Res.,* 8: 4057 (1980), which is incorporated herein by reference), the PLtetO-1 and Plac/are-1 promoters (Lutz and Bujard, *Nucleic Acids Res.,* 25: 1203-1210 (1997), which is incorporated herein by reference), and hybrid promoters such as the tac promoter (deBoer et al., *Proc. Natl. Acad. Sci. USA,* 80: 21-25 (1983), which is incorporated herein by reference).

In some embodiments, the heterologous nucleic acid described herein is operably linked to a promoter. In some embodiments, the promoter is a constitutive promoter. In some embodiments, the promoter is an inducible promoter. An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent may comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof. Appropriate environmental inducers can include, but are not limited to, exposure to heat (i.e., thermal pulses or constant heat exposure), various steroidal compounds, divalent cations (including $Cu^{2+}$ and $Zn^{2+}$), galactose, tetracycline, IPTG (isopropyl-β-D thiogalactoside), as well as other naturally occurring and synthetic inducing agents and gratuitous inducers.

Inducible promoters useful in the methods and systems as disclosed herein also include those that are repressed by "transcriptional repressors" that are subject to inactivation by the action of environmental, external agents, or the product of another gene. Such inducible promoters may also be termed "repressible promoters" where it is required to distinguish between other types of promoters in a given module or component of the biological switch converters described herein. Preferred repressors for use in the present invention are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause the dissociation of the tet repressor from the engineered promoter and allow transcription of the sequence downstream of the engineered promoter to occur.

A bacterial cell for use in the methods and compositions described herein can be any of any species. Preferably, the bacterial cells are of a species and/or strain which is amenable to culture and genetic manipulation. In some embodiments, the bacterial cell is a Gram-positive bacterial cell. In some embodiments, the bacterial cell is a Gram-negative bacterial cell. In some embodiments, the parental strain of the bacterial cell of the technology described herein can be a strain optimized for protein expression. Non-limiting examples of bacterial species and strains suitable for use in the present technologies include *Escherichia coli, E. coli* BL21, *E. coli* Tuner, *E. coli* Rosetta, *E. coli* JM101, and derivatives of any of the foregoing. Bacterial strains for protein expression are commercially available, e.g. EXPRESS™ Competent *E. coli* (Cat. No. C2523; New England Biosciences; Ipswich, Mass.). In some embodiments, the cell is an *E. coli* cell.

In some embodiments, the bacterium expresses wild-type CsgA. In some embodiments, the bacterium comprises a mutation and/or deletion in the wild-type CsgA gene, e.g., such that the cell does not express wild-type CsgA. In some embodiments, the heterologous nucleic acid described herein is introduced into a bacterial cell by homologous recombination, e.g., such that the heterologous nucleic acid replaces an endogenous csgA gene in the bacterial genome.

In one aspect, provided herein is a method for producing a recombinant silk protein comprising culturing an engineered bacterium described herein under conditions suitable for the expression of the recombinant silk protein in the engineered bacterium. In some embodiments, the recombinant silk protein is secreted from the engineered bacterium. In some embodiments, the methods comprise collecting the recombinant silk protein from the cell culture medium comprising the engineered bacterium or in which the engineered bacterium was cultured.

In some embodiments, the engineered bacterium is not exposed to a lysing agent prior to collecting the recombinant protein from the cell culture medium. In some embodiments, the recombinant polypeptide is collected from a supernatant of the cell culture medium. Methods for collecting a recombinant polypeptide from a cell culture medium are well known in the art, and include, for example, filtration, centrifugation, dialysis, ultrafiltration, and lyophilization.

In some embodiments, the methods of producing a recombinant polypeptide described herein further comprise purifying the recombinant polypeptide. Recombinant polypeptides can also be isolated from cellular lysates and/or cell culture medium by using any standard technique known in the art. For example, recombinant polypeptides can be engineered to comprise an epitope tag such as a poly-histidine tag or other polypeptide tag such as myc or FLAG. Purification can be achieved by immunoprecipitation using antibodies specific to the recombinant peptide (or any epitope tag comprised in the amino sequence of the recombinant polypeptide) or by running the lysate solution or cell culture medium through an affinity column that comprises a matrix for the polypeptide or for any epitope tag comprised in the recombinant polypeptide (see for example, Ausubel et al., eds. (1993) Current Protocols in Molecular Biology, Section 10.11.8, John Wiley & Sons, New York).

Other methods for purifying a recombinant polypeptide include, but are not limited to ion exchange chromatography, hydroxylapatite chromatography, hydrophobic interaction chromatography, preparative isoelectric focusing chromatography, molecular sieve chromatography, HPLC, native gel electrophoresis in combination with gel elution, affinity chromatography, and preparative isoelectric. See, e.g., Marston et al. (1990) *Meth. Enz.,* 182:264-275.

In another aspect, the present disclosure provides a recombinant silk protein as described herein. In some embodiments, the recombinant silk protein is produced using the methods described herein. In some embodiments, the recombinant silk protein comprises a periplasmic translocation signal sequence, an outer membrane signal sequence and a silk fibroin domain. In some embodiments, the recombinant silk protein comprises an outer membrane signal sequence and a silk fibroin domain. In some embodiments, the recombinant silk protein comprises an periplasmic translocation signal sequence and a silk fibroin domain. In some embodiments, the recombinant silk protein comprises a silk fibroin domain. In some embodiments, the recombinant silk protein comprises a periplasmic translocation signal sequence, an outer membrane signal sequence, a silk fibroin domain, and one or more of an amyloid domain (e.g., CsgA), an elastin domain, and a collagen domain. In some embodiments, the recombinant silk protein comprises an outer membrane signal sequence, a silk fibroin domain, and one or more of an amyloid domain (e.g., CsgA), an elastin domain, and a collagen domain. In some embodiments, the recombinant silk protein comprises a periplasmic translocation signal sequence, a silk fibroin domain, and one or more of an amyloid domain (e.g., CsgA), an elastin domain, and a collagen domain. In some embodiments, the recombinant silk protein comprises a silk fibroin domain, and one or more of an amyloid domain (e.g., CsgA), an elastin domain, and a collagen domain. In some embodiments, the recombinant silk protein further comprises a functional protein selected from the group consisting of an enzyme, an antibody and a detectable protein. In some embodiments, the detectable protein is selected from the group consisting of poly-histidine tag, a myc tag, a FLAG tag, a hemagglutinin (HA) tag, and a V5 tag. In some embodiments, the recombinant polypeptide comprises a protease cleavage site amino acid sequence.

In another aspect, provided herein is a curli fiber comprising a plurality of recombinant silk proteins as described herein. In some embodiments, the curli fiber comprises a plurality of recombinant silk proteins, wherein the plurality of silk proteins comprise a silk fibroin domain and an amyloid domain. In some embodiments, the curli fiber comprises a plurality of recombinant silk proteins, wherein the plurality of silk proteins comprise a periplasmic translocation signal sequence, an outer membrane signal sequence, a silk fibroin domain, an amyloid domain (e.g., CsgA), and optionally, one or more of an elastin domain, and a collagen domain. In some embodiments, the curli fiber comprises a plurality of recombinant silk proteins, wherein the plurality of silk proteins comprise an outer membrane signal sequence, a silk fibroin domain, an amyloid domain (e.g., CsgA), and optionally, one or more of an elastin domain, and a collagen domain. In some embodiments, the curli fiber comprises a plurality of recombinant silk proteins, wherein the plurality of silk proteins comprise a periplasmic translocation signal sequence, a silk fibroin domain, an amyloid domain (e.g., CsgA), and optionally, one or more of an elastin domain, and a collagen domain. In some embodiments, the curli fiber comprises a plurality of recombinant silk proteins, wherein the plurality of silk proteins comprise a silk fibroin domain, an amyloid domain (e.g., CsgA), and optionally, one or more of an elastin domain, and a collagen domain. In some embodiments, the curli fiber comprises a plurality of recombinant silk proteins, wherein the plurality of silk proteins further comprises a functional protein selected from the group consisting of an enzyme, an antibody and a detectable protein. In some embodiments, the detectable protein is selected from the group consisting of poly-histidine tag, a myc tag, a FLAG tag, a hemagglutinin (HA) tag, and a V5 tag. In some embodiments, the curli fiber comprises a plurality of recombinant silk proteins, wherein the plurality of silk proteins comprise a protease cleavage site amino acid sequence.

In one aspect, provided herein is a biofilm comprising an engineered bacterium described herein, e.g., an engineered bacterium comprising a heterologous nucleic acid encoding a recombinant silk protein, wherein the recombinant silk protein comprises a periplasmic translocation signal sequence, an outer membrane secretion signal sequence, and a silk fibroin domain. In another aspect, provided herein is a biofilm comprising a cell comprising one or more engineered CsgA polypeptide and/or comprising a vector or nucleic acid encoding such a polypeptide.

In another aspect, provided herein is a biofilm comprising a curli fiber formed from a plurality of recombinant silk proteins as described herein. In some embodiments, the biofilm comprises a curli fiber formed from a plurality of recombinant silk proteins, wherein the recombinant silk proteins comprise a silk fibroin domain and an amyloid domain.

As used herein, a "biofilm" refers to a mass of microorganisms which can adhere or is adhering to a surface. A biofilm comprises a matrix of extracellular polymeric substances, including, but not limited to extracellular DNA, proteins, glycopeptides, and polysaccharides. The nature of a biofilm, such as its structure and composition, can depend on the particular species of bacteria present in the biofilm. Bacteria present in a biofilm are commonly genetically or phenotypically different than corresponding bacteria not in a biofilm, such as isolated bacteria or bacteria in a colony.

In some embodiments, the technology described herein relates to a biofilm that is produced by culturing an engineered bacterium described herein under conditions suitable for the production of a biofilm. Conditions suitable for the production of a biofilm can include, but are not limited to, conditions under which the microbial cell is capable of logarithmic growth and/or polypeptide synthesis. Conditions may vary depending upon the species and strain of microbial cell selected. Conditions for the culture of microbial cells are well known in the art. Biofilm production can also be induced and/or enhanced by methods well known in the art, e.g. contacting cells with subinhibitory concentrations of beta-lactam or aminoglycoside antibiotics, exposing cells to fluid flow, contacting cells with exogenous poly-N-acetylglucosamine (PNAG), or contacting cells with quorum sensing signal molecules. In some embodiments, conditions suitable for the production of a biofilm can also include conditions which increase the expression and secretion of CsgA, e.g., by exogenously expressing CsgD. In some embodiments, the biofilm can comprise the bacterium which produced the biofilm. In some embodiments, described herein is a composition comprising an engineered CsgA polypeptide which includes CsgA attached to a polypeptide such as spider silk, as described herein.

When expressed by a bacterium capable of forming curli, e.g. a bacterium expressing CsgA, CsgB, CsgC, CsgD, CsgE, CsgF, and CsgG or some subset thereof, CsgA units will be assembled to form curli filaments, e.g., polymeric chains of CsgA or of a recombinant silk protein comprising an amyloid domain as described herein. In some embodiments, filaments of the polypeptide can be present in the composition. In some embodiments, the filaments can be part of a proteinaceous network, e.g., multiple filaments which can be, e.g., interwoven, overlapping, and/or in contact with each other. In some embodiments, the proteinaceous network can comprise additional biofilm components, e.g., materials typically found in an $E.\ coli$ biofilm. Non-limiting examples of biofilm components can include biofilm proteins (e.g. FimA, FimH, Ag43, AidA, and/or TibA) and/or non-proteinaceous biofilm components (e.g. cellulose, PGA and/or colonic acid). In some embodiments, the composition can further comprise a cell comprising an engineered CsgA polypeptide and/or comprising a vector or nucleic acid encoding such a polypeptide.

Definitions of common terms in cell biology and molecular biology can be found in The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol.152, S. L. Berger and A. R. Kimmel Eds., Academic Press Inc., San Diego, USA (1987); and Current Protocols in Protein Science (CPPS) (John E. Coligan, et. al., ed., John Wiley and Sons, Inc.), which are all incorporated by reference herein in their entireties.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The following examples are set forth as being representative of the present disclosure. These examples are not to be construed as limiting the scope of the present disclosure as these and other equivalent embodiments will be apparent in view of the present disclosure, figures and accompanying claims.

EXAMPLE I

Genetic Construction of Silk Gene Constructs

Protein motifs of dragline silk from *Nephila clavipes* (Golden Silk Orb-weaving spider) were synthetically synthesized and concatenated using molecular biology techniques to create silk domains and amyloid-silk domain fusions that are secreted through the T8SS functional amyloid secretion pathway of *E. coli*. Additional consensus dragline silk sequences are set forth in SEQ ID NOs:2054-2074.

Figure 2:
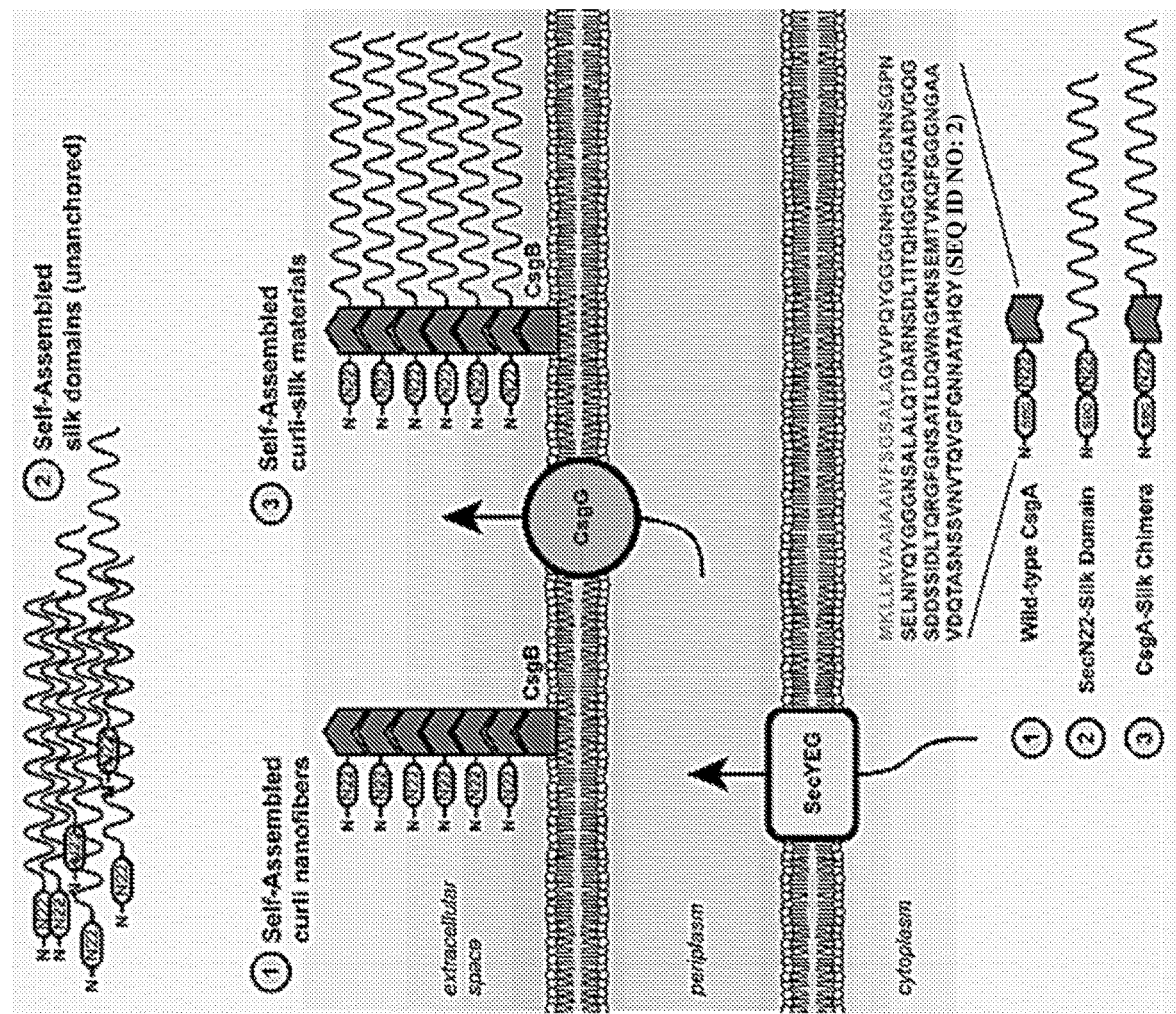
FIG. 2 depicts in schematic secretion of silk product using the T8SS bacterial functional amyloid secretion system.
Figure 3B:
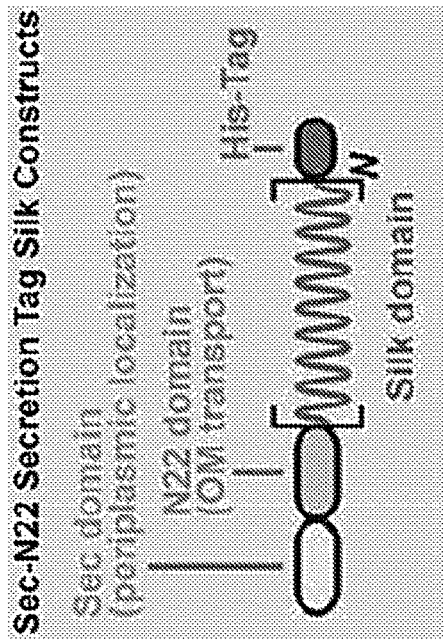
Figure 3B:
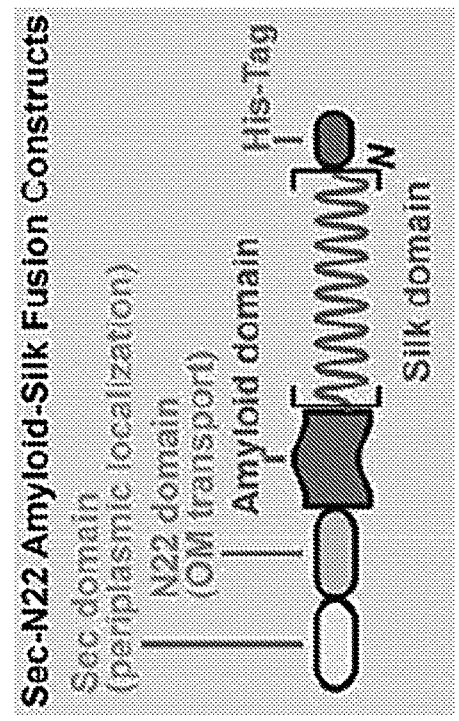

Spider silk from the Golden Silk Orb-weaving spider *Nephila clavipes* has been extensively studied for its mechanical properties. The major protein constituent of dragline silk from *N. clavipes* is the major ampullate spidroin-1 (MaSp1). The repetitive domain of the silks is a repeated protein motif that influences its resulting mechanical properties. As depicted in FIGS. 3A and 3B, the repetitive 35-amino acid peptide motif was used as the 'silk domain' in the constructs, which were synthetized and engineered into fusion proteins containing 4, 8, 16, 32, and 64 head-to-tail repeating domains, ranging in size from 17-202 amino acids. To test the ability of these constructs to be secreted from the cells via the T8SS pathway, a N-terminal tag was added consisting of the CsgA signal sequence, consisting of a 20-amino acid Sec sequence for periplasmic localization and a 22-amino acid N22 domain which directs the protein to the CsgG/CsgE outer membrane complex for secretion. A second set of fusion constructs with the full CsgA protein located N-terminal to the silk domain, resulting in bifunctional self-assembling silks, was also tested for secretion. See FIG. 2.

Figure 6A:
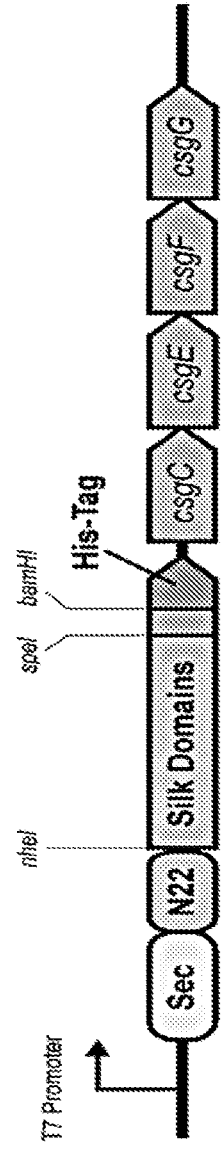
FIG. 6A-6C are schematics showing constructs described herein.
Figure 6B:
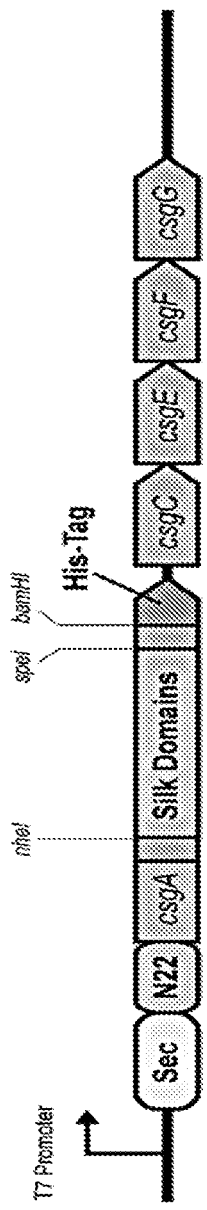
Figure 6C:
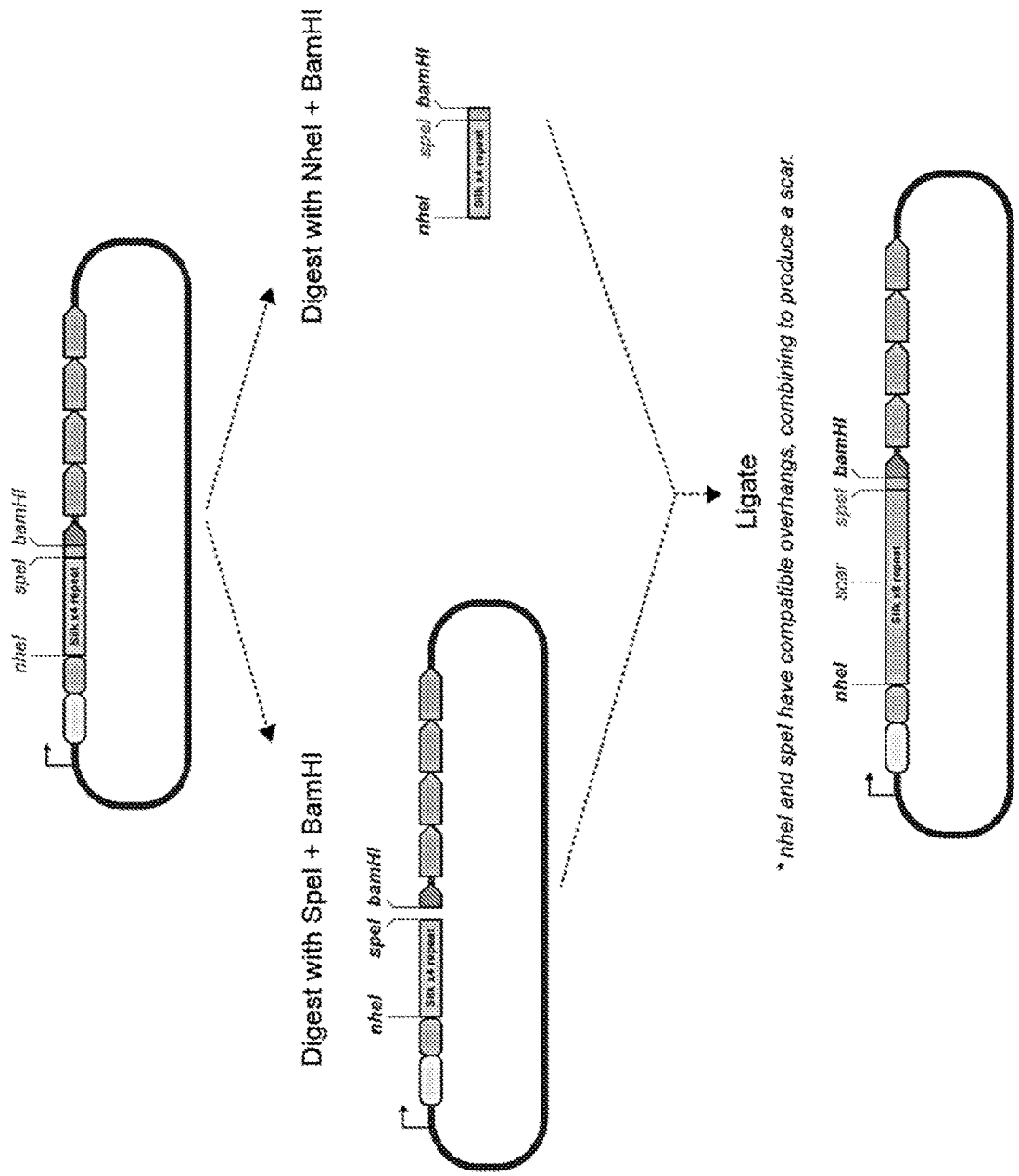
Figure 7:
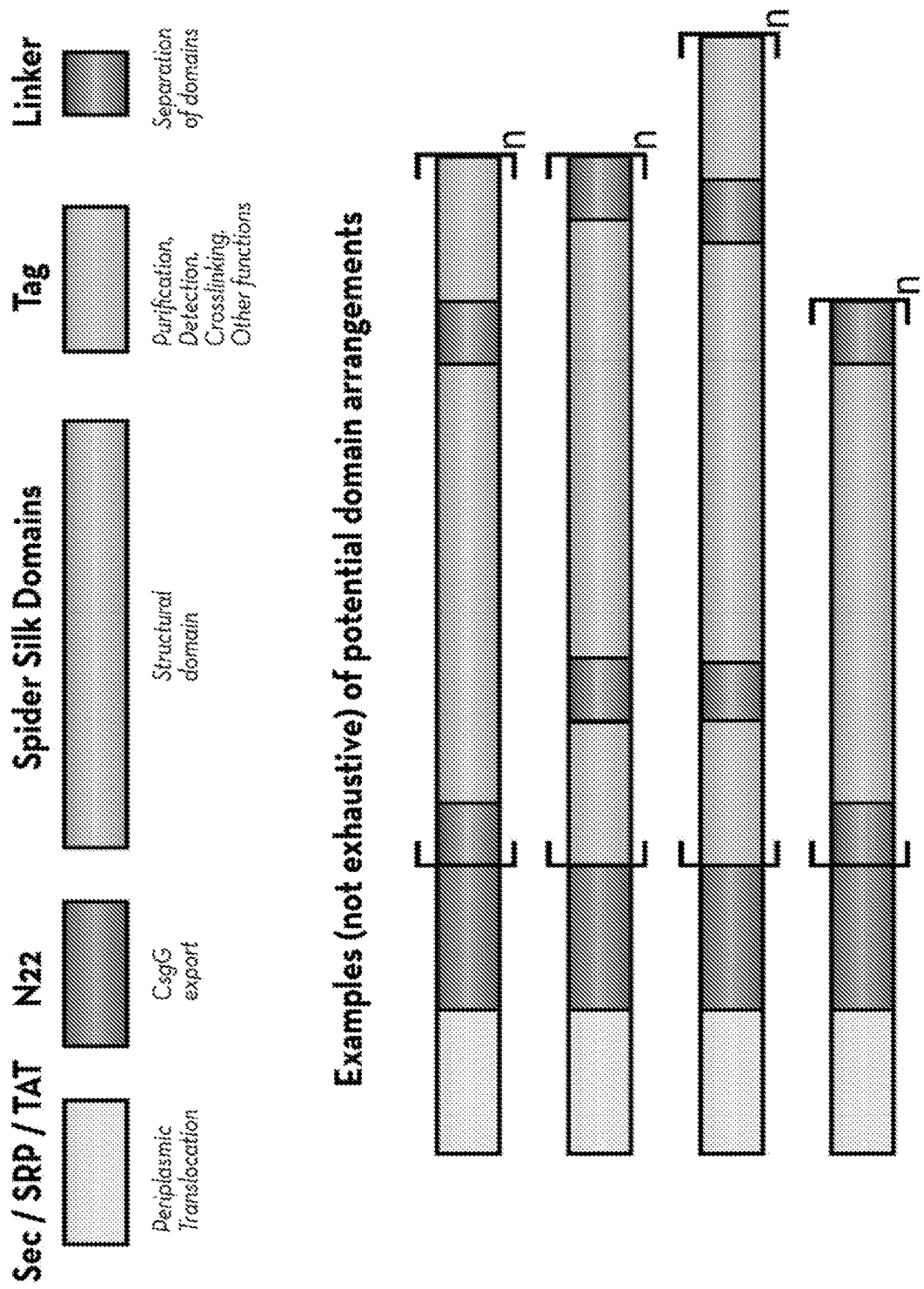
FIG. 7 schematically represents domain arrangements of potential domain arrangements of recombinant silk proteins described herein.

More specifically, and with reference to FIG. 6, the gene for the major ampullate spidroin 1 spider silk protein from *Nephila clavipes* was computationally codon optimized for *Escherichia coli* expression from the know protein sequence (see Xu, M., & Lewis, R. V. (1990) Structure of a protein superfiber: spider dragline silk. *Proc. Natl. Acad. Sci.* USA, 87(18), 7120-7124, hereby incorporated by reference in its entirety.

Using this optimized gene sequence, a 4-mer containing four consecutive repeats of the spider silk domain was ordered as a synthetic DNA construct with flanking restriction sites which allowed head-to-tail concatenation through molecular biology cloning to generate longer proteins with repeating spider silk domains. This is advantageous as the molecular weight of the spider silk proteins directly correlates with the physical properties of the spider silk. See Xia, X.-X., Qian, Z.-G., Ki, C. S., Park, Y. H., Kaplan, D. L., & Lee, S. Y. (2010). Native-sized recombinant spider silk protein produced in metabolically engineered *Escherichia coli* results in a strong fiber. *Proc. Natl. Acad. Sci.* USA 107(32), 14059-14063, hereby incorporated by reference in its entirety.

The 4-mer repeat, herein referred to as Silk4, was created with an N-terminal NheI restriction site. Immediately following the Silk4 domain, the construct was engineered with a multiple cloning site consisting of SpeI-KpnI-BamHI, a 6×-histidine tag, and finally, a stop codon. The final plasmid was inserted into pET30a-ACEFG plasmid, which contains 5 genes of the wildtype curli operon, csgA, csgC, csgE, csgF, and csgG. For the spider silk only constructs, the Silk4 construct was inserted in place of the CsgA curlin domains, resulting in a Sec-N22 tagged Silk4 construct. For the spider silk-CsgA fusions, the Silk4 construct was cloned behind the csgA gene to create a fusion protein containing the native CsgA protein, a -GSGGSG-linker, and the Silk4 construct.

To generate expression constructs containing various amounts of spider silk domains, the designed restriction sites were used in a concatenation strategy to generate Silk8 (8 consecutive domains), Silk16 (16 consecutive domains), Silk32 (32 consecutive domains), and Silk64 (64 consecutive domains). Briefly, the Silk4 constructs were digested by NheI and BamHI and the Silk4 dropout was isolated. Also, the Silk4 constructs were digested by SpeI and BamHI and the major linearized plasmid was isolated. The dropout was ligated into the digested plasmid. Since NheI and SpeI have compatible overhangs, they combine to generate a "scar" in which two concatenated Silk4 domains are linked by nucleotides encoding for an -AS-linker. This resulting plasmid, containing 8 total spider silk domains, was named Silk8. The remaining signal sequence only and CsgA fusion constructs were cloned in a similar manner.

EXAMPLE II

Expression of Spider Silk Domains Using the CsgA (Sec-N22) Signal Sequence

For the experiments shown herein, the Rosetta-gami 2(DE3) cell lines from Novagen, which are pET vector compatible, were used. The constructs here could also be cloned into other plasmid systems and other *E. coli* strains. To test the transformed cells for spider silk expression, LB plates were made with the proper plasmid selectable marker and supplemented with 30 µg/mL of Congo red dye and 0.05 mM IPTG. Congo red has been shown to bind to silk, and any extracellularly produced silk will bind to the dye. See Slotta, U., Hess, S., SpieB, K., Stromer, T., Serpell, L., & Scheibel, T. (2007). Spider Silk and Amyloid Fibrils: A Structural Comparison. *Macromolecular Bioscience*, 7(2), 183-188, hereby incorporated by reference in its entirety.

All transformants were grown in LB media with antibiotic and 0.5% glucose overnight at room temperature, pelleted, and then resuspended in LB to an OD600 of 0.5. This culture was then spotted onto the LB—Congo red agar plates, allowed to dry, and then incubated at 25° C. for 48 hours before imaging.

Figure 4:
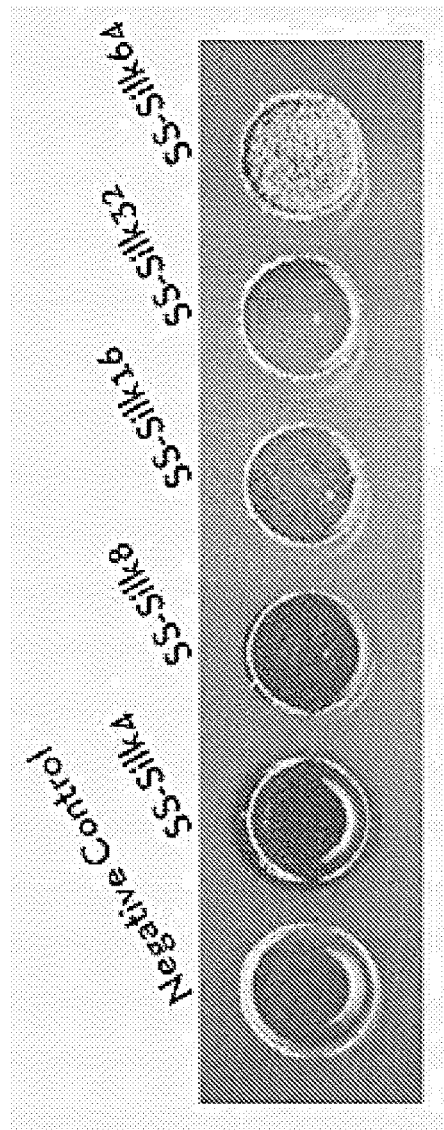
FIG. 4 illustrates that Sec-N22-[Silk]$_N$-HisTag constructs are secreted by the *E. coli* T8SS pathway. SS-Silk constructs transformed into *E. coli* and plated onto Congo Red LB plates and induced with 0.05 mM IPTG. The negative control plasmid encodes for a non-CR binding protein, BSA.

Spider silk domain repeats were cloned in front of the CsgA signal sequence, which includes a Sec translocation sequence for periplasmic localization and the N22 sequence, which is a CsgG-specific signal for transport through the outer membrane. The transformants were grown and spotted onto LB plates containing Congo red, a red dye which has been shown to bind to silk, as illustrated in FIG. 4. See dos Santos-Pinto, J. R. A. et al. Structural Model for the Spider Silk Protein Spidroin-1. *J. Proteome Res.* 150811080734002 (2015) hereby incorporated by reference in its entirety. Since these silk domains are not tethered to the cell surface, one would expect to see a red halo around the spotted cells as the silk proteins diffuse through the agar and bind to the dye, especially for constructs of a lower molecular weight. This was observed for SS-Silk4 and, to a lesser extent, the SS-Silk8 spots. As depicted in FIG. 3A, Sec-N22-[Silk]$_N$-HisTag constructs are secreted by the *E. coli* T8SS pathway. SS-Silk constructs transformed into *E. coli* and plated onto Congo Red LB plates and induced with 0.05 mM IPTG. The negative control plasmid encodes for a non-CR binding protein, BSA. See FIGS. 3A and 3B. Various Sec-N22 secretion tag constructs were tested, as shown in Table 1. Various Sec-N22 amyloid-silk fusion constructs were tested, as shown in Table 2.

TABLE 1

SEC-N22 SECRETION TAG SILK CONSTRUCTS

| CONSTRUCT | GENE SIZE (BP) | PROTEIN SIZE (RESIDUES) | MOLECULAR WEIGHT (KDA) |
|---|---|---|---|
| SS-Silk4 | 474 | 198 | 17.29 |
| SS-Silk8 | 900 | 339 | 28.91 |
| SS-Silk16 | 1752 | 621 | 52.14 |
| SS-Silk32 | 3456 | 1185 | 98.61 |
| SS-Silk64 | 6864 | 2313 | 191.55 |

TABLE 2

SEC-N22 AMYLOID-SILK FUSION CONSTRUCTS

| CONSTRUCT | GENE SIZE (BP) | PROTEIN SIZE (RESIDUES) | MOLECULAR WEIGHT (KDA) |
|---|---|---|---|
| SS-Silk4 | 474 | 198 | 17.29 |
| SS-Silk8 | 900 | 339 | 28.91 |
| SS-Silk16 | 1752 | 621 | 52.14 |
| SS-Silk32 | 3456 | 1185 | 98.61 |
| SS-Silk64 | 6864 | 2313 | 191.55 |

EXAMPLE III

Expression of Spider Silk Domains as a Fusion to the CsgA Protein

Figure 5:
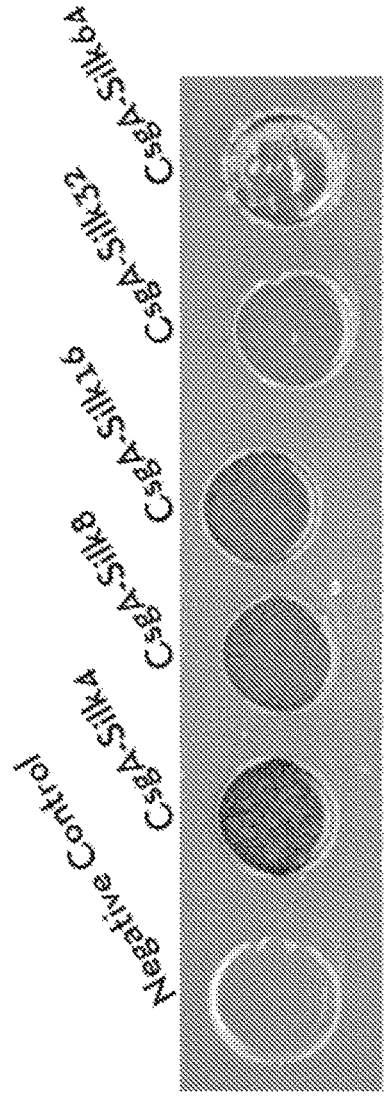
FIG. 5 illustrates that Sec-N22-CsgA-[Silk]$_N$-HisTag constructs are secreted by the *E. coli* T8SS pathway. SS-Silk constructs transformed into *E. coli* and plated onto Congo Red LB plates and induced with 0.05 mM IPTG. The negative control plasmid encodes for a non-CR binding protein, BSA.

To determine if silk-protein fused to different functional proteins could be secreted to generate a programmable silk material, CsgA-silk domain fusions were tested. As depicted in FIG. 3B, these constructs also contain the Sec-N22 T8SS secretion signal domains. These CsgA-silk fusions would assemble extracellularly into a hybrid amyloid-silk material. See FIG. 2. These constructs, when expressed in *E. coli* and spotted onto LB-CR plates, show clear Congo Red binding, indicating successful secretion of these silk-protein fusions. See FIG. 5.

FIG. 3B depicts the Sec-N22-CsgA-[Silk]$_N$-HisTag constructs secreted by the *E. coli* T8SS pathway. The fusion proteins were transformed into *E. coli* and plated onto Congo Red LB plates and induced with 0.05 mM IPTG. The negative control plasmid encodes for a non-CR binding protein, BSA. See FIGS. 3A and 3B.

EXAMPLE IV

Additional Applications

Aspects of the present disclosure utilize the modified bacterial cells which express a silk protein or a CsgA-silk fusion. Silks have been intensely researched for its potential use in a plethora of different applications. As it can be assembled into different forms (fibers, thin films, foams, etc.) the applications are likewise varied. Methods described herein decrease processing costs for silk proteins. A small sampling of the commercial applications for silk proteins products are listed in the table below. In addition, other anticipated applications of the disclosed production process may include: use in a manufacturing process for the production of various silk proteins for use in high performance textiles (e.g., sporting wear, protective armor, etc.), hydrogels, films, or foams, or biomedical devices. Use in combination with optimized curli secretion systems in other engineered strains of *E. coli*. In vivo production of silk-based materials (e.g., in the GI tract) for therapeutic or diagnostic purposes. Production of silk-based materials in agricultural settings, such as on the surface of leaves, plants, roots, or in soil. Uses are shown in Table 3.

TABLE 3

APPLICATIONS

| TYPE OF FABRICATION | MARKET | APPLICATION |
|---|---|---|
| Fibers | Industrial | Super-tough fabrics and composites[6, 18] |
| Fibers | Industrial | Large-scale 3D printed structures[1] |
| Fibers | Biomedical | Functionalized superior sutures and medical bandages[20, 21] |
| Fibers | Biomedical | Artificial biomimetic muscles[22] |
| Foams | Biomedical | Biomaterials for tissue bioengineering scaffolds[23, 24] |
| Foams | Biomedical | Injectable tetrahertz waveguides[25] |
| Thin Films | Industrial | Transparent photonic films[26] |
| Thin Films | Industrial/Biomedical | Biocompatible flexible electrodes[27] |
| Thin Films | Biomedical | Brain electrode coatings[28] |
| Thin Films | Biomedical | Drug storage and delivery[29] |
| Thin Films | Biomedical | Vaccine stabilization[30] |
| Thin Films | Biomedical | Antibiotic stabilization[30] |
| Thin Films | Biomedical | Virus stabilization[31] |
| Thin Films | Biomedical | Enzyme stabilization[32] |
| Films | Industrial/Biomedical | Microfluidic devices[33] |
| Particles/Spheres | Biomedical | Drug storage and delivery[34-36] |
| Particles/Spheres | Industrial | Battery energy storage materials[36] |

REFERENCES

Each of the following references is hereby incorporated by reference in its entirety.

1. Griffiths, J. R. & Salanitri, V. R. The strength of spider silk. *J. Mater. Sci.* 15, 491-496 (1980).
2. Gosline, J. M., Guerette, P. a, Ortlepp, C. S. & Savage, K. N. The mechanical design of spider silks: from fibroin sequence to mechanical function. *J. Exp. Biol.* 202, 3295-3303 (1999).
3. Huang, X., Liu, G. & Wang, X. New secrets of spider silk: Exceptionally high thermal conductivity and its abnormal change under stretching. *Adv. Mater.* 24, 1482-1486 (2012).
4. Guan, J., Vollrath, F. & Porter, D. Two mechanisms for supercontraction in Nephila spider dragline silk. *Biomacromolecules* 12, 4030-4035 (2011).
5. Fahnestock, S. R. & Irwin, S. L. Synthetic spider dragline silk proteins and their production in *Escherichia coli*. *Appl. Microbiol. Biotechnol.* 47, 23-32 (1997).
6. Xia, X.-X. et al. Native-sized recombinant spider silk protein produced in metabolically engineered *Escherichia coli* results in a strong fiber. *Proc. Natl. Acad. Sci.* 107, 14059-14063 (2010).
7. Widmaier, D. M. et al. Engineering the Salmonella type III secretion system to export spider silk monomers. *Mol. Syst. Biol.* 5, 1-9 (2009).
8. Fahnestock, S. R. & Bedzyk, L. A. Production of synthetic spider dragline silk protein in Pichia pastoris. *Appl. Microbiol. Biotechnol.* 47, 33-9 (1997).
9. Yang, J., Barr, L. A., Fahnestock, S. R. & Liu, Z.-B. High yield recombinant silk-like protein production in transgenic plants through protein targeting. *Transgenic Res.* 14, 313-24 (2005).
10. Lazaris, A. Spider Silk Fibers Spun from Soluble Recombinant Silk Produced in Mammalian Cells. *Science (80-.).* 295, 472-476 (2002).
11. Keten, S., Xu, Z., Ihle, B. & Buehler, M. J. Nanoconfinement controls stiffness, strength and mechanical toughness of β-sheet crystals in silk. *Nat. Mater.* 9, 359-367 (2010).
12. Nova, A., Keten, S., Pugno, N. M., Redaelli, A. & Buehler, M. J. Molecular and nanostructural mechanisms of deformation, strength and toughness of spider silk fibrils. *Nano Lett.* 10, 2626-34 (2010).
13. Chapman, M. R. et al. Role of *Escherichia coli* curli operons in directing amyloid fiber formation. *Science* 295, 851-855 (2002).
14. Desvaux, M., Hébraud, M., Talon, R. & Henderson, I. R. Secretion and subcellular localizations of bacterial proteins: a semantic awareness issue. *Trends Microbiol.* 17, 139-45 (2009).
15. Sivanathan, V. & Hochschild, A. Generating extracellular amyloid aggregates using *E. coli* cells. *Genes Dev.* 26, 2659-2667 (2012).
16. Widmaier, D. M. & Voigt, C. a. Quantification of the physiochemical constraints on the export of spider silk proteins by Salmonella type III secretion. *Microb. Cell Fact.* 9, 78 (2010).
17. dos Santos-Pinto, J. R. A. et al. Structural Model for the Spider Silk Protein Spidroin-1. *J. Proteome Res.* 150811080734002 (2015). doi:10.1021/acs.jproteome.5b00243.
18. Heidebrecht, A. et al. Biomimetic Fibers Made of Recombinant Spidroins with the Same Toughness as Natural Spider Silk. *Adv. Mater.* 4, 1-6 (2015).
19. Schacht, K. et al. Biofabrication of cell-loaded 3D spider silk constructs. *Angew. Chem. Int. Ed. Engl.* 54, 2816-20 (2015).
20. Chen, X. et al. Antibacterial Surgical Silk Sutures Using a High-Performance Slow-Release Carrier Coating System. *ACS Appl. Mater. Interfaces* 7, 22394-403 (2015).
21. Calamak, S., Erdogdu, C., Ozalp, M. & Ulubayram, K. Silk fibroin based antibacterial bionanotextiles as wound dressing materials. *Mater. Sci. Eng. C. Mater. Biol. Appl.* 43, 11-20 (2014).
22. Agnarsson, I., Dhinojwala, A., Sahni, V. & Blackledge, T. a. Spider silk as a novel high performance biomimetic muscle driven by humidity. *J. Exp. Biol.* 212, 1990-1994 (2009).
23. Wang, S., Ghezzi, C. E., White, J. D. & Kaplan, D. L. Coculture of dorsal root ganglion neurons and differentiated human corneal stromal stem cells on silk-based scaffolds. *J. Biomed. Mater. Res. A* 103, 3339-48 (2015).
24. Yao, D., Liu, H. & Fan, Y. Silk scaffolds for musculoskeletal tissue engineering. *Exp. Biol. Med. (Maywood).* (2015). doi:10.1177/1535370215606994.
25. Guerboukha, H., Yan, G., Skorobogata, O. & Skorobogatiy, M. Silk Foam Terahertz Waveguides. *Adv. Opt. Mater.* n/a-n/a (2014). doi:10.1002/adom.201400228.
26. Perry, H., Gopinath, A., Kaplan, D. L., Negro, L. D. & Omenetto, F. G. Nano- and micropatterning of optically transparent, mechanically robust, biocompatible silk fibroin films. *Adv. Mater.* 20, 3070-3072 (2008).
27. Kim, D.-H. et al. Dissolvable films of silk fibroin for ultrathin conformal bio-integrated electronics. *Nat. Mater.* 9, 511-7 (2010).
28. Tien, L. W. et al. Silk as a multifunctional biomaterial substrate for reduced glial scarring around brain-penetrating electrodes. *Adv. Funct. Mater.* 23, 3185-3193 (2013).
29. Yucel, T., Lovett, M. L. & Kaplan, D. L. Silk-based biomaterials for sustained drug delivery. *J. Control. Release* 190, 381-97 (2014).
30. Zhang, J. et al. Stabilization of vaccines and antibiotics in silk and eliminating the cold chain. *Proc. Natl. Acad. Sci. U.S.A.* 109, 11981-6 (2012).
31. Sutherland, T. D. et al. Stabilization of viruses by encapsulation in silk proteins. *ACS Appl. Mater. Interfaces* 6, 18189-96 (2014).
32. Lu, Q. et al. Stabilization and release of enzymes from silk films. *Macromol. Biosci.* 10, 359-68 (2010).
33. Bettinger, C. J. et al. Silk Fibroin Microfluidic Devices. *Adv. Mater.* 19, 2847-2850 (2007).
34. Tian, Y., Jiang, X., Chen, X., Shao, Z. & Yang, W. Doxorubicin-loaded magnetic silk fibroin nanoparticles for targeted therapy of multidrug-resistant cancer. *Adv. Mater.* 26, 7393-8 (2014).
35. Qu, J. et al. Silk fibroin nanoparticles prepared by electrospray as controlled release carriers of cisplatin. *Mater. Sci. Eng. C. Mater. Biol. Appl.* 44, 166-74 (2014).
36. Sheng, W. et al. Silk-regulated hierarchical hollow magnetite/carbon nanocomposite spheroids for lithium-ion battery anodes. *Nanotechnology* 26, 115603 (2015).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11365225B2). An electronic copy of the "Sequence Listing" will also be available from the USPTO upon request and payment of the fee set forth in 37 CFR 1.19(b)(3).

The invention claimed is:

1. A method of producing an engineered *Escherichia coli* (*E. coli*) bacterium comprising
    introducing into an *E. coli* bacterium an exogenous nucleic acid encoding a recombinant protein comprising a Sec domain for periplasmic localization, an N22 domain for directing the recombinant protein to the outer membrane for secretion, and at least one silk fibroin domain comprising the amino acid sequence set forth in SEQ ID NO:3; wherein the *E. coli* bacterium has at least one genomic nucleic acid encoding a Type VIII polypeptide secretion system; and wherein the exogenous nucleic acid is under operation of a promoter to express the recombinant protein.

2. The method of claim 1, wherein the polypeptide secretion system is a HlyA Type 1 secretion system.

3. The method of claim 1, wherein the polypeptide secretion system includes a periplasmic secretion system and a system for secretion through the outer membrane of the bacterium.

4. The method of claim 1, wherein the polypeptide secretion system includes a periplasmic secretion system and a system for secretion through the outer membrane of the bacterium and the domain for periplasmic localization is a Tat domain or a signal recognition particle domain.

5. The method of claim 1, wherein the polypeptide secretion system includes a periplasmic secretion system and a system for secretion through the outer membrane of the bacterium and wherein the domain for directing the recombinant protein to the outer membrane for secretion is a YebF domain.

6. The method of claim 1, wherein the exogenous nucleic acid further encodes the recombinant protein to include a CsgA domain.

7. The method of claim 1, wherein the silk fibroin domain comprises 4 to 64 repeats of the amino acid sequence set forth in SEQ ID NO:3.

8. The method of claim 1, wherein the exogenous nucleic acid further encodes the recombinant protein to include one or more functional proteins comprising an enzyme, an antibody or a detectable protein.

\* \* \* \* \*